US012239557B2

(12) United States Patent
Okumura et al.

(10) Patent No.: US 12,239,557 B2
(45) Date of Patent: Mar. 4, 2025

(54) DRUG SUPPLY DEVICE

(71) Applicant: OLYMPUS CORPORATION, Tokyo (JP)

(72) Inventors: Takuya Okumura, Tokyo (JP); Shunsuke Motosugi, Tokyo (JP); Shinji Takahashi, Tokyo (JP); Hiroyuki Morishita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1205 days.

(21) Appl. No.: 17/022,814

(22) Filed: Sep. 16, 2020

(65) Prior Publication Data

US 2020/0405518 A1   Dec. 31, 2020

Related U.S. Application Data

(63) Continuation of application No. PCT/JP2018/014660, filed on Apr. 6, 2018.

(51) Int. Cl.
*A61F 2/958*  (2013.01)
*A61B 17/00*  (2006.01)
(Continued)

(52) U.S. Cl.
CPC ........ *A61F 2/958* (2013.01); *A61B 17/00234* (2013.01); *A61B 17/12136* (2013.01);
(Continued)

(58) Field of Classification Search
CPC ...... A61F 2/958; A61F 2/90; A61F 2002/045; A61F 2002/075; A61B 17/12168; A61B 17/12136
See application file for complete search history.

(56) References Cited

U.S. PATENT DOCUMENTS 4,600,015 A * 7/1986 Evans .................... A61B 5/037
  604/920
5,645,560 A   7/1997 Crocker et al.
(Continued)

FOREIGN PATENT DOCUMENTS

EP   2 298 250 A1   3/2011
EP   2 508 222 A1   10/2012
(Continued)

OTHER PUBLICATIONS

Japanese Office Action dated May 31, 2022 received in 2021-115851.
(Continued)

*Primary Examiner* — Nathan R Price
*Assistant Examiner* — Haden Matthew Ritchie
(74) *Attorney, Agent, or Firm* — Scully, Scott, Murphy & Presser, P.C.

(57) ABSTRACT

A drug supply device includes: a tube body; a first expansion member configured to be expanded to a first outer diameter and a second expansion member configured to be expanded to a second outer diameter that is greater than the first outer diameter, the first expansion member and the second expansion member being positioned on a distal-end side of the tube body; and a masking member that extends between the expansion members and that is connected to outer surfaces of the expansion members at two ends thereof. The tube body includes an outlet that opens between the expansion members and a channel that is in communication with the outlet, the masking member is formed in an arc shape in a lateral cross-section that is orthogonal to the longitudinal axis, and the masking member stretches between the expansion members in a state in which the expansion members are expanded.

19 Claims, 20 Drawing Sheets

(51) Int. Cl.
*A61B 17/12* (2006.01)
*A61B 90/00* (2016.01)
*A61F 2/90* (2013.01)
*A61M 25/10* (2013.01)

(52) U.S. Cl.
CPC .... *A61B 90/08* (2016.02); *A61B 2017/00296* (2013.01); *A61B 2017/00827* (2013.01); *A61B 17/12045* (2013.01); *A61B 17/12168* (2013.01); *A61B 2090/0811* (2016.02); *A61M 2025/105* (2013.01)

(56) References Cited

U.S. PATENT DOCUMENTS

| | | |
|---|---|---|
| 5,707,355 A | 1/1998 | Zimmon |
| 5,843,116 A | 12/1998 | Crocker et al. |
| 5,906,587 A | 5/1999 | Zimmon |
| 6,027,486 A | 2/2000 | Crocker et al. |
| 6,098,629 A | 8/2000 | Johnson et al. |
| 6,338,345 B1 | 1/2002 | Johnson et al. |
| 6,401,718 B1 | 6/2002 | Johnson et al. |
| 6,488,653 B1 | 12/2002 | Lombardo |
| 6,500,171 B1 | 12/2002 | Maguire et al. |
| 6,500,174 B1 | 12/2002 | Maguire et al. |
| 6,544,226 B1 | 4/2003 | Gaiser et al. |
| 6,575,896 B2 | 6/2003 | Silverman et al. |
| 7,185,657 B1 | 3/2007 | Johnson et al. |
| 8,926,602 B2* | 1/2015 | Pageard ............... A61B 18/02 606/21 |
| 2002/0148475 A1 | 10/2002 | Johnson et al. |
| 2002/0198521 A1 | 12/2002 | Maguire |
| 2003/0183962 A1 | 10/2003 | Buiser et al. |
| 2003/0233150 A1 | 12/2003 | Bourne et al. |
| 2003/0236535 A1 | 12/2003 | Onuki et al. |
| 2004/0087936 A1 | 5/2004 | Stern et al. |
| 2005/0096673 A1 | 5/2005 | Stack et al. |
| 2005/0247320 A1 | 11/2005 | Stack et al. |
| 2006/0247610 A1 | 11/2006 | Lanphere et al. |
| 2007/0060932 A1 | 3/2007 | Stack et al. |
| 2007/0135822 A1 | 6/2007 | Onuki et al. |
| 2007/0260112 A1 | 11/2007 | Rahmani |
| 2007/0260178 A1 | 11/2007 | Skerven et al. |
| 2007/0276432 A1 | 11/2007 | Stack et al. |
| 2008/0015523 A1 | 1/2008 | Baker |
| 2008/0065122 A1 | 3/2008 | Stack et al. |
| 2009/0018602 A1 | 1/2009 | Mitelberg et al. |
| 2009/0240105 A1 | 9/2009 | Smit et al. |
| 2010/0168512 A1 | 7/2010 | Rahmani |
| 2010/0174306 A1 | 7/2010 | Mitelberg et al. |
| 2010/0217151 A1 | 8/2010 | Gostout et al. |
| 2010/0241146 A1 | 9/2010 | Stack et al. |
| 2011/0028784 A1* | 2/2011 | Patil ................... A61B 17/3423 600/106 |
| 2011/0038938 A1 | 2/2011 | Ison et al. |
| 2011/0230718 A1 | 9/2011 | Akui |
| 2011/0257622 A1 | 10/2011 | Salahieh et al. |
| 2012/0095395 A1 | 4/2012 | Haery |
| 2012/0226300 A1 | 9/2012 | Mitelberg et al. |
| 2012/0226302 A1 | 9/2012 | Mitelberg et al. |
| 2012/0259401 A1 | 10/2012 | Gerrans et al. |
| 2013/0012863 A1 | 1/2013 | Stack et al. |
| 2013/0197554 A1 | 8/2013 | Skerven et al. |
| 2013/0345670 A1 | 12/2013 | Rajagopalan et al. |
| 2014/0010847 A1 | 1/2014 | Lin |
| 2014/0121585 A1 | 5/2014 | Baker et al. |
| 2014/0249465 A1 | 9/2014 | Stack et al. |
| 2015/0025313 A1 | 1/2015 | Baker et al. |
| 2015/0032087 A1 | 1/2015 | Shibata et al. |
| 2015/0157358 A1 | 6/2015 | Mitelberg et al. |
| 2015/0352334 A1 | 12/2015 | Haery |
| 2015/0374352 A1 | 12/2015 | Inoue |
| 2016/0213890 A1 | 7/2016 | Kaufman et al. |
| 2016/0262867 A1 | 9/2016 | Baker et al. |
| 2016/0296675 A1 | 10/2016 | Longo et al. |
| 2016/0310200 A1 | 10/2016 | Wang |
| 2017/0035595 A1 | 2/2017 | Stack et al. |
| 2018/0015264 A1 | 1/2018 | Wang et al. |
| 2018/0296806 A1 | 10/2018 | Haery |
| 2019/0038881 A1 | 2/2019 | Wang et al. |
| 2019/0076283 A1 | 3/2019 | Okumura et al. |
| 2019/0269493 A1 | 9/2019 | Okumura et al. |
| 2019/0269494 A1 | 9/2019 | Okumura et al. |
| 2019/0298476 A1 | 10/2019 | Okumura et al. |
| 2020/0360026 A1* | 11/2020 | Horton ............ A61B 17/12136 |

FOREIGN PATENT DOCUMENTS

| | | |
|---|---|---|
| EP | 3 141 192 A1 | 3/2017 |
| JP | 2000-500673 A | 1/2000 |
| JP | 2000-509304 A | 7/2000 |
| JP | 2002-538932 A | 11/2002 |
| JP | 2002-540838 A | 12/2002 |
| JP | 2003-507096 A | 2/2003 |
| JP | 2003-526460 A | 9/2003 |
| JP | 2004-000601 A | 1/2004 |
| JP | 2005-521476 A | 7/2005 |
| JP | 2007-508053 A | 4/2007 |
| JP | 2008-526461 A | 7/2008 |
| JP | 2009-533150 A | 9/2009 |
| JP | 2009-536083 A | 10/2009 |
| JP | 2010-533036 A | 10/2010 |
| JP | 2014-508580 A | 4/2014 |
| JP | 2014-521390 A | 8/2014 |
| JP | 2014-171629 A | 9/2014 |
| JP | 2014-188205 A | 10/2014 |
| JP | 2015-023904 A | 2/2015 |
| JP | 2015-033634 A | 2/2015 |
| JP | 2015-066144 A | 4/2015 |
| JP | 2016-032523 A | 3/2016 |
| JP | 2016-154927 A | 9/2016 |
| JP | 2016-185296 A | 10/2016 |
| JP | 2017-533036 A | 11/2017 |
| JP | 2018-504209 A | 2/2018 |
| WO | 1997/018008 A1 | 5/1997 |
| WO | 97/40877 A1 | 11/1997 |
| WO | 00/56237 A2 | 9/2000 |
| WO | 00/59398 A1 | 10/2000 |
| WO | 01/12255 A1 | 2/2001 |
| WO | 01/68015 A1 | 9/2001 |
| WO | 03/082359 A1 | 10/2003 |
| WO | 2005/037152 A1 | 4/2005 |
| WO | 2006/078672 A1 | 7/2006 |
| WO | 2007/120727 A1 | 10/2007 |
| WO | 2007/131112 A2 | 11/2007 |
| WO | 2009/009274 A2 | 1/2009 |
| WO | 2011/046002 A1 | 4/2011 |
| WO | 2012/054387 A2 | 4/2012 |
| WO | 2012/099974 A2 | 7/2012 |
| WO | 2012/162114 A1 | 11/2012 |
| WO | 2015/016162 A1 | 2/2015 |
| WO | 2016/070032 A1 | 5/2016 |
| WO | 2016/118923 A1 | 7/2016 |
| WO | 2016/158290 A1 | 10/2016 |

OTHER PUBLICATIONS

U.S. Office Action dated Sep. 9, 2019 received in U.S. Appl. No. 15/942,617.

International Search Report dated Jul. 3, 2018 received in PCT/JP2018/014660.

U.S. Office Action dated Mar. 16, 2020 received in U.S. Appl. No. 15/942,617.

U.S. Office Action dated Apr. 16, 2020 received in U.S. Appl. No. 15/704,198.

U.S. Office Action dated Aug. 3, 2020 received in U.S. Appl. No. 15/942,617.

* cited by examiner

DRUG SUPPLY DEVICE

CROSS-REFERENCE TO RELATED APPLICATIONS

This is a continuation of International Application PCT/JP2018/014660 which is hereby incorporated by reference herein in its entirety.

TECHNICAL FIELD

The present invention relates to a drug supply device.

BACKGROUND ART

In the related art, known methods for treating gastroesophageal reflux disease, which is a benign disease caused by a decrease in the function of the cardiac sphincter at the entrance of the stomach, include, for example, methods described in Patent Literatures 1 and 2. With the method described in Patent Literature 1, tissue is removed from the surface of the digestive tract, such as in the esophagus, the stomach, or the like, and a pathway inside the body is reconstructed by means of a healing reaction. In addition, in Patent Literature 2, at the gastroesophageal junction or the stomach, an incision is made in at least one of a mucosal layer and a submucosa, and stenosis is caused in the digestive tract due to scarring.

CITATION LIST

Patent Literature

{PTL 1} Japanese Translation of PCT International Application, Publication No. 2009-536083
{PTL 2} U.S. patent application, Publication No. 2015/0374352, Specification

SUMMARY OF INVENTION

A first aspect of the present invention is a drug supply device including: a tube body having a longitudinal axis; a first expansion member configured to be expanded to a first outer diameter and a second expansion member configured to be expanded to a second outer diameter that is greater than the first outer diameter of the first expansion member, the first expansion member and the second expansion member being positioned on a distal-end side of the tube body and disposed with a spacing between each other in a direction along the longitudinal axis; and a masking member that includes a distal-end portion and a proximal-end portion, that extends along the longitudinal axis between the first expansion member and the second expansion member, in which the proximal-end portion is connected to an outer surface of the first expansion member, and in which the distal-end portion is connected to an outer surface of the second expansion member, wherein the tube body includes an outlet that opens between the first expansion member and the second expansion member and a channel that is in communication with the outlet and through which a liquid drug passes, the masking member is formed in an arc shape in a lateral cross-section that is orthogonal to the longitudinal axis, and, in a state in which the first expansion member and the second expansion member are expanded, the masking member stretches between the first expansion member and the second expansion member.

A second aspect of the present invention is a drug supply device including: an expansion member that includes a distal end, a proximal end, and a center axis extending between the distal end and the proximal end, and that is configured to be expanded in a radial direction that is orthogonal to the center axis; and a drug sheet that is provided on an outer surface of the expansion member and that holds a drug, wherein the expansion member includes a first expansion region and a second expansion region that is positioned farther on a distal-end side than the first expansion region is and that is continuous with the first expansion region, and a second outer diameter of the second expansion region in an expanded state is greater than a first outer diameter of the first expansion region in an expanded state, and the drug sheet is provided in an area that bridges across a distal-end portion of the first expansion region and a proximal-end portion of the second expansion region and that does not reach an entire circumference about the center axis in the outer surface of the expansion member.

A third aspect of the present invention is a drug supply device including: an expansion member that includes a distal end, a proximal end, and a center axis extending between the distal end and the proximal end, and that is configured to be expanded in a radial direction that is orthogonal to the center axis; a mesh member that is disposed outside the expansion member so as to form a gap with respect to an outer surface of the expansion member and that covers the outer surface of the expansion member; and a channel that includes an outlet that opens into the gap, that is in communication with the outlet, and through which a liquid drug passes, wherein the expansion member includes a first expansion region and a second expansion region that is positioned farther on a distal-end side than the first expansion region is and that is continuous with the first expansion region, and an outer diameter of the second expansion region in an expanded state is greater than an outer diameter of the first expansion region in an expanded state, the mesh member includes a plurality of small holes that open in an outer surface of the mesh member and that are in communication with the gap, and the plurality of small holes are provided in an area that bridges across a distal-end portion of the first expansion region and a proximal-end portion of the second expansion region and that does not reach an entire circumference about the center axis in the outer surface of the mesh member.

DESCRIPTION OF EMBODIMENTS

First Embodiment

A drug supply device 1 according to a first embodiment of the present invention and a method for causing stenosis of the digestive tract by using the same will be described below with reference to the drawings.

FIGS. 1A to 10 show a method for using the drug supply device 1 according to this embodiment. As shown in FIGS. 1A to 10, the drug supply device 1 is used in a procedure for causing stenosis in a target region by means of a liquid drug such as ethanol in the treatment of gastroesophageal reflux disease or the like. The target region is a portion of a region extending to the cardia D from the gastroesophageal junction C (lower portion of the esophagus) in the inner wall of the digestive tract. The gastroesophageal junction C is a portion in which the esophagus (digestive tract) A connects to the stomach B. Reference sign E indicates the pylorus.

Figure 1A:
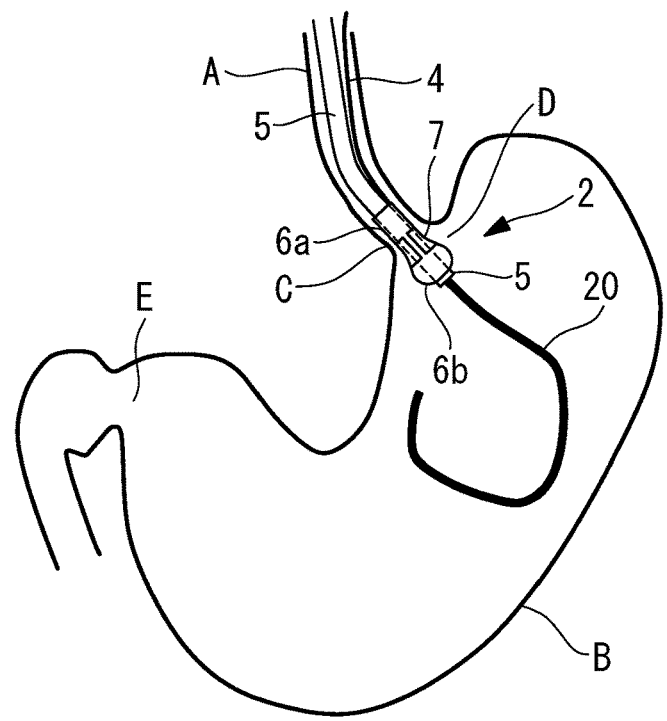
FIG. 1A is a diagram for explaining a method for causing stenosis of the digestive tract, by employing a drug supply device according to a first embodiment of the present invention.
Figure 1B:
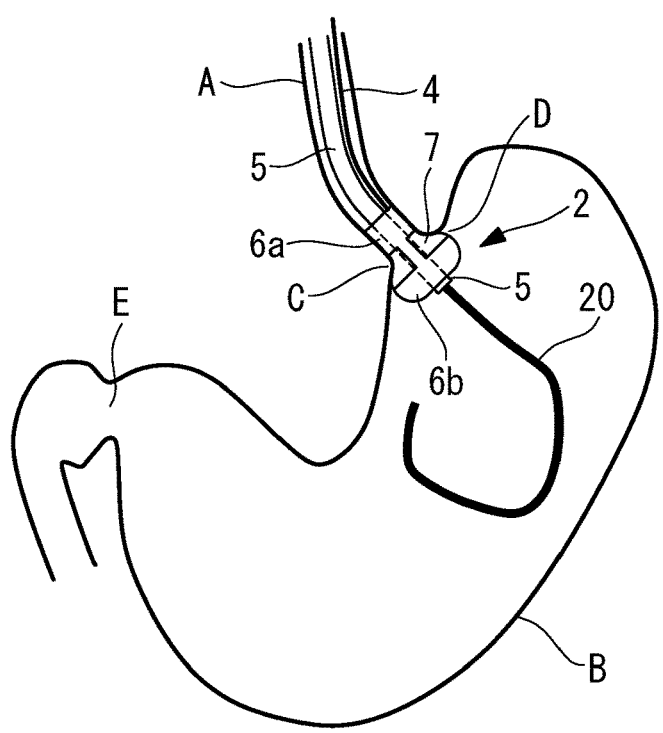
FIG. 1B is a diagram for explaining the method for causing stenosis of the digestive tract, by employing the drug supply device according to the first embodiment of the present invention.
Figure 1C:
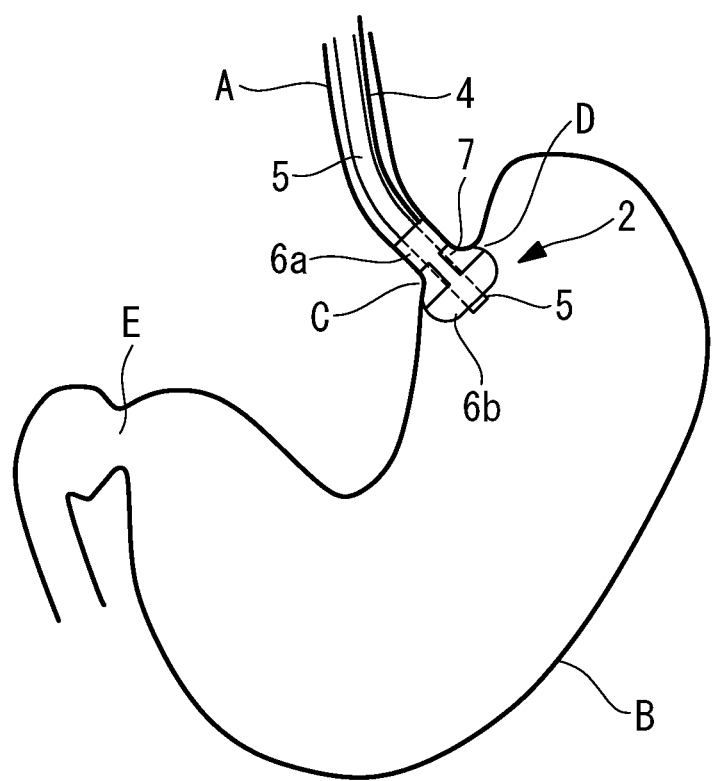
FIG. 1C is a diagram for explaining the method for causing stenosis of the digestive tract, by employing the drug supply device according to the first embodiment of the present invention.
Figure 2:
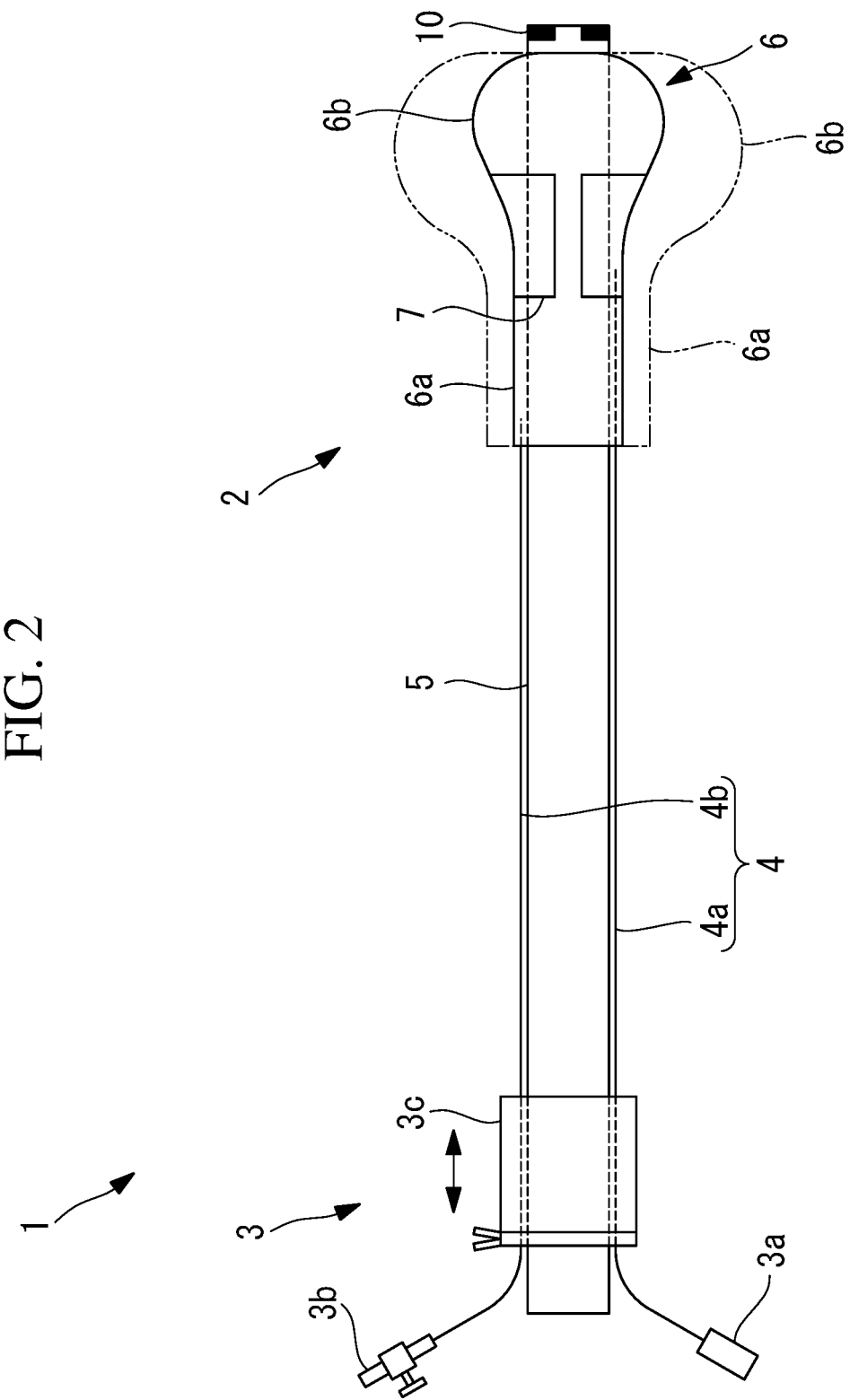
FIG. 2 is an overall configuration diagram of the drug supply device according to the first embodiment of the present invention.

As shown in FIG. 2, the drug supply device 1 includes: a distal-end treating portion 2; a proximal-end operating portion 3; and a first tube principal body 4 that connects the distal-end treating portion 2 and the proximal-end operating portion 3.

The distal-end treating portion 2 includes: a second tube principal body (tube body) 5 into which an insertion portion 20 of a flexible endoscope can be inserted; an expansion member 6 that is secured to an outer circumferential surface of a distal-end portion of the second tube principal body 5; and a drug sheet 7 provided at a substantially center portion of the expansion member 6.

The second tube principal body 5 has an inner diameter that is greater than an outer diameter of the insertion portion 20 of the endoscope, and, inside the second tube principal body 5, the insertion portion 20 of the endoscope can be moved in a longitudinal direction and can be rotated about a longitudinal axis.

The expansion member 6 is, for example, a balloon. The expansion member 6 has a distal end, a proximal end, and a center axis that extends between the distal end and the proximal end. The second tube principal body 5 passes through the expansion member 6 along the center axis of the expansion member 6, and the expansion member 6 is provided around the entire circumference of the second tube principal body 5.

The expansion member 6 has a first expansion region 6a and a second expansion region 6b that is positioned farther on a distal-end side than the first expansion region 6a is and that is continuous with the first expansion region 6a. Each of the first expansion region 6a and the second expansion region 6b can be elastically deformed between a contracted shape, indicated by the solid line in FIG. 2, and an expanded shape, indicated by the two-dot chain line in FIG. 2, as a result of being expanded and contracted in a radial direction that is orthogonal to the center axis.

In the state in which the first and second expansion regions 6a and 6b are contracted, the outer diameter of the expansion member 6 as a whole is smaller than the inner diameter of the esophagus A. The first expansion region 6a can be expanded to an outer diameter that is equivalent to or greater than the inner diameter of the esophagus A. The second expansion region 6b can be expanded to an outer diameter that is even greater than the expanded first expansion region 6a. In a state in which the expansion regions 6a and 6b are expanded, the expansion member 6 has a maximum diameter in the second expansion region 6b.

The drug sheet 7 is provided in an area bridging across a distal-end portion of the first expansion region 6a and a proximal-end portion of the second expansion region 6b in a direction along the center axis of the expansion member 6. The drug sheet 7 is formed of a sheet-like porous member in which a liquid drug can be impregnated, for example, a sponge or a non-woven fabric. The liquid drug is supplied to the drug sheet 7 via the first tube principal body 4, the drug sheet 7 holds the drug as a result of the drug sheet 7 being impregnated with the drug, and the drug is supplied to the tissue that is in contact with the drug sheet 7. The drug sheet 7 is provided in an area that does not reach the entire circumference of the expansion member 6 in a circumferential direction around the center axis, and it is preferable that the drug sheet 7 be provided in an area that corresponds to 60-80% of the entire circumference of the expansion member 6. The drug sheet 7 may be expandable in the circumferential direction in accordance with expansion and contraction of the expansion member 6.

On a distal-end side of the second expansion region 6b, a marker 10 that extends in the circumferential direction about the center axis and that indicates the position of the drug sheet 7 is provided. The marker 10 is provided at the same position as that of the drug sheet 7 in the circumferential direction about the center axis. The marker 10 may be provided at the distal-end portion of the second tube principal body 5 that protrudes from the second expansion region 6b, or the marker 10 may be provided on a surface of the second expansion region 6b on the distal-end side thereof.

The proximal-end operating portion 3 includes a drug-supplying port 3a to which a syringe (not shown) can be connected and an air-feeding port 3b to which an inflator (not shown) can be connected.

The proximal-end operating portion 3 additionally includes a mouthpiece 3c equipped with a clamp. The mouthpiece 3c can be secured with respect to the second tube principal body 5 at an arbitrary position.

The first tube principal body 4 includes a liquid feeding tube 4a and an air feeding tube 4b.

The liquid feeding tube 4a extends to the drug sheet 7 without opening to an interior space in the expansion member 6, and a distal-end opening of the liquid feeding tube 4a is connected to the drug sheet 7. A proximal-end opening of the liquid feeding tube 4a is in communication with the drug-supplying port 3a. By connecting a syringe containing the drug to the drug-supplying port 3a, it is possible to supply the drug to the drug sheet 7 via the liquid feeding tube 4a from the syringe.

A distal-end opening of the air feeding tube 4b opens into the interior space in the expansion member 6. A proximal-end opening of the air feeding tube 4b is in communication with the air-feeding port 3b. By connecting an inflator to the air-feeding port 3b and by supplying a fluid to the expansion member 6 via the air feeding tube 4b from the inflator, it is possible to expand the expansion member 6. The air-feeding port 3b is provided with a two-way stopcock that can be switched between a closed state and an open state. By switching the two-way stopcock to the closed state after expanding the expansion member 6, it is possible to maintain the shape of the expanded expansion member 6.

The specific configuration of the first tube principal body 4 is not limited to the plurality of tubes 4a and 4b that are independent of each other.

For example, the first tube principal body 4 may be a multi-lumen tube having a plurality of lumens that are provided at independent positions with respect to each other. In this case, one lumen is a liquid feeding lumen (drug supply pathway) that extends to the drug sheet 7 without opening to the interior space in the expansion member 6 and in which a distal-end opening thereof is connected to the drug sheet 7. The other lumen is an air feeding lumen that opens to the interior space in the expansion member 6.

Next, a method for causing stenosis of the digestive tract by using the drug supply device 1 will be described.

Figure 3:
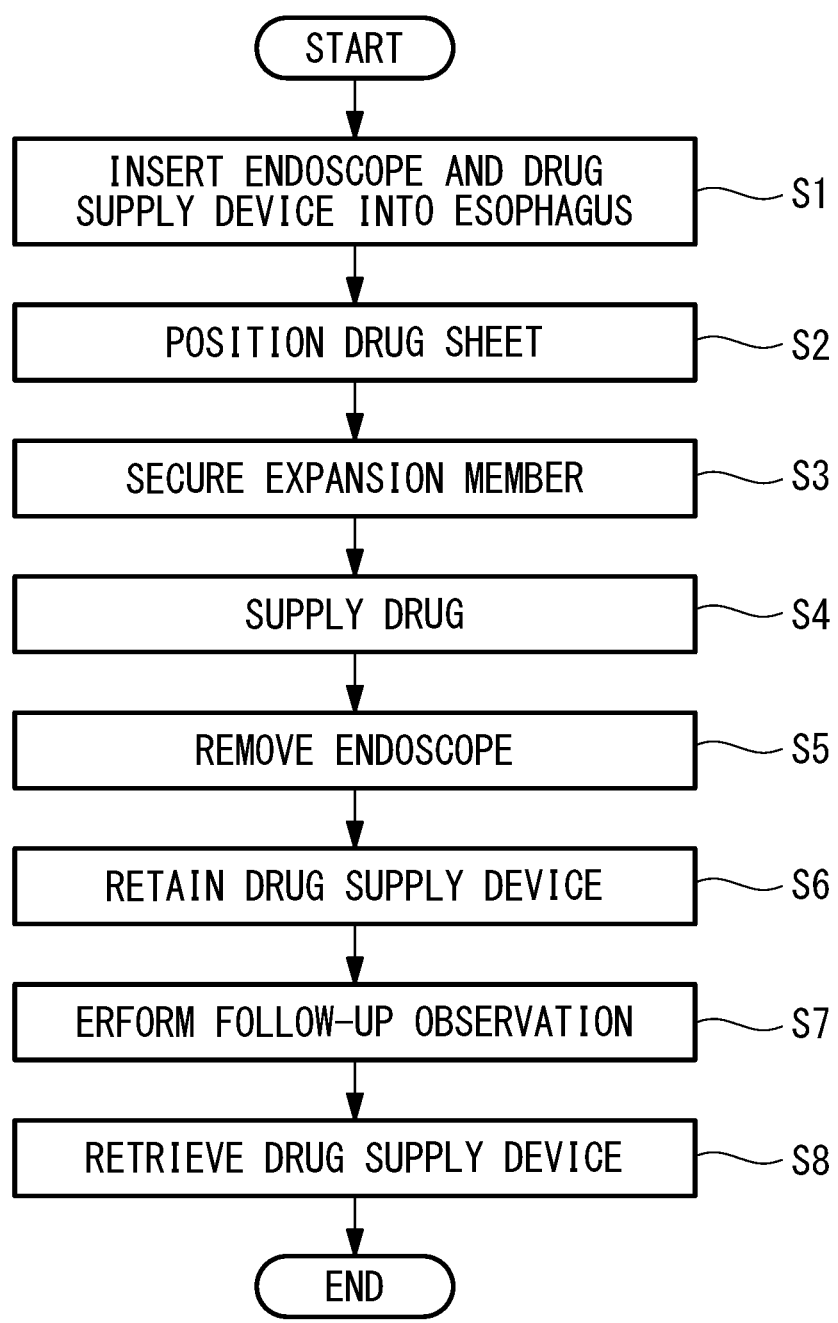
FIG. 3 is a flowchart showing the method according to the first embodiment of the present invention for causing stenosis of the digestive tract.

As shown in FIG. 3, the method according to this embodiment for causing stenosis of the digestive tract includes: an inserting step S1 of orally inserting the drug supply device 1 and the insertion portion 20 of the endoscope into the esophagus A; a positioning step S2 of positioning the drug sheet 7 with respect to a target region to which the drug is to be supplied, while observing the region by using the endoscope; a securing step S3 of securing the expansion member 6 with respect to the inner wall of the esophagus A; a drug supplying step S4 of supplying the drug to the target region; a removing step S5 of removing the insertion portion 20 to the exterior of the body from the esophagus A; a retaining step S6 of placing the expansion member 6 in the esophagus A for a prescribed retaining period; a follow-up observation step S7 of checking the state of the expansion member 6 by using the endoscope; and a retrieving step S8 of retrieving the drug supply device 1 from inside the esophagus A.

In the inserting step S1, the insertion portion 20 of the endoscope is inserted into the second tube principal body 5 of the drug supply device 1 in advance. Then, the drug supply device 1 is inserted into the digestive tract from the mouth of the subject together with the endoscope. Note that the drug supply device 1 may be inserted into the digestive tract while placing the second tube principal body 5 along the insertion portion 20 of the endoscope after inserting the endoscope into the digestive tract from the mouth of the subject. Next, a bending portion provided at a distal-end portion of the insertion portion 20 of the endoscope is bent by about 180° inside the stomach B, thereby looking up the esophagus A from the stomach B. Next, while observing the surface of a mucosal layer of the relaxed digestive tract (for example, the gastroesophageal junction C) by using the endoscope, an area of the target region is identified on the surface of the mucosal layer. A target region R is an area set to be smaller than the entire circumference in a portion of a region extending to the cardia D from the gastroesophageal junction C (esophagus lower portion) so as not to cause excessive stenosis. It is preferable that the target region R be an area corresponding to 60-80% of the entire circumference and extending toward the bottom portion of the stomach from a lesser-curvature side.

Next, in the positioning step S2, the drug sheet 7 is positioned with respect to the target region R by means of an advancing/retracting operation of the drug supply device 1 and a rotating operation thereof about the longitudinal axis so that the drug sheet 7 faces the target region R.

Specifically, by connecting the inflator to the air-feeding port 3b of the operating portion 3 and by supplying a gas into the expansion member 6 from the inflator via the first tube principal body 4, the first expansion region 6a and the second expansion region 6b are expanded until the outer diameter of the second expansion region 6b becomes greater than the inner diameter of the cardia D. Next, the insertion portion 20 and the second tube principal body 5 are moved toward the proximal end until reaching a position at which the expanded second expansion region 6b abuts against the cardia D. By doing so, the drug sheet 7 bridging across the first expansion region 6a and the second expansion region 6b is positioned with respect to the target region in the vicinity of the gastroesophageal junction C in the longitudinal direction of the esophagus A.

Figure 4:
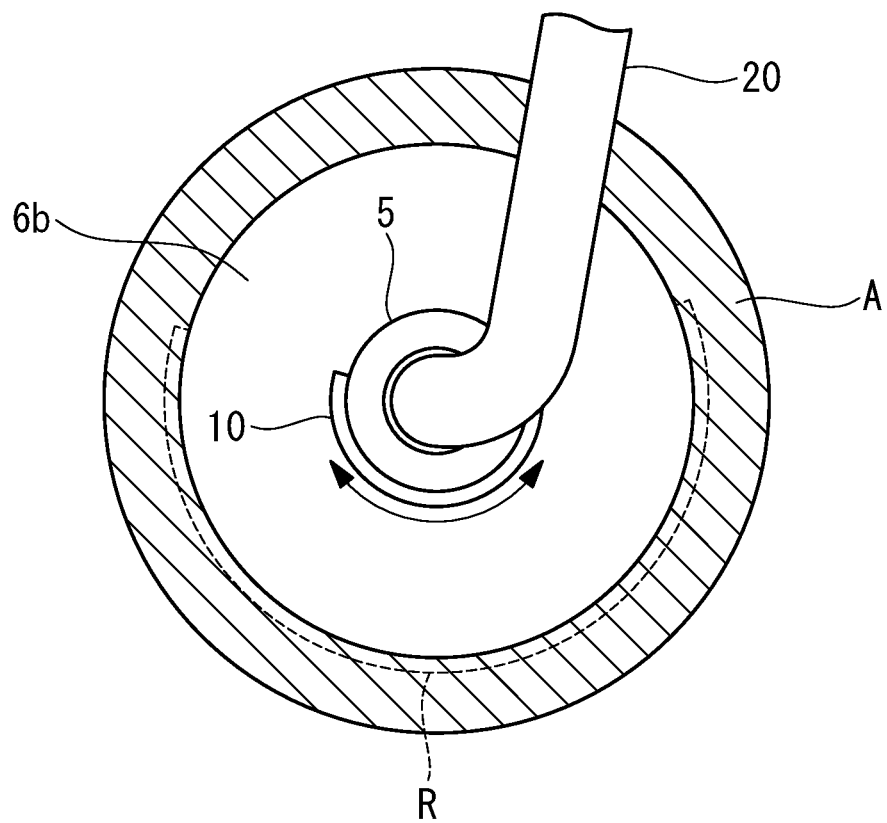
FIG. 4 is a diagram for explaining a positioning step in FIG. 3, and is a diagram in which a treating portion disposed at the gastroesophageal junction is viewed from the stomach side.

Next, by twisting the second tube principal body 5 about the longitudinal axis, the drug sheet 7 is positioned with respect to the target region R in the circumferential direction of the esophagus A. When doing so, it is not possible to directly observe the drug sheet 7 by using the endoscope, because the expanded second expansion region 6b blocks the view; however, as shown in FIG. 4, it is possible to observe the marker 10, which is provided in the second expansion region 6b on the opposite side from the first expansion region 6a, by using the endoscope. Therefore, a surgeon can position the drug sheet 7 with respect to the target region R by indirectly checking the position of the drug sheet 7 in the circumferential direction on the basis of the marker 10.

Next, in the securing step S3, after confirming that the drug sheet 7 has been positioned in the target region R in the positioning step S2, the mouthpiece 3c is slid to be secured to the mouth of the subject. Accordingly, the distal-end treating portion 2 is secured at a certain position, and the position of the drug sheet 7 is secured with respect to the target region R.

Next, in the drug supplying step S4, the syringe containing the drug is connected to the drug-supplying port 3a, and the drug is supplied to the drug sheet 7 from the syringe via the liquid feeding tube 4a of the first tube principal body 4. The drug impregnates the drug sheet 7 and is supplied to the target region R that is in firm contact with the drug sheet 7.

Next, in the removing step S5, the endoscope is removed to the exterior of the body while leaving the drug supply device 1 inside the esophagus A.

Next, in the retaining step S6, the drug supply device 1 is retained in the esophagus A for a prescribed period, for example, two days. The expansion member 6 is secured at a certain position with respect to the longitudinal direction of the esophagus A by means of the mouthpiece 3c, which is equipped with a clamp, and rotation thereof about the center axis is also restricted. Therefore, the expansion member 6 is prevented from being moved in the longitudinal direction of the esophagus A or rotated in the circumferential direction thereof due to peristalsis of the esophagus A and gravity during the retaining period, thus maintaining the firm contact state between the drug sheet 7 and the target region R. Accordingly, the drug is continuously supplied to the target region R during the retaining period.

Next, in the follow-up observation step S7, the insertion portion 20 of the endoscope is inserted into the stomach B again, and it is confirmed, by means of the endoscope, that the expansion member 6 remains secured with respect to the inner wall and that the expansion member 6 is still at the position at which the expansion member 6 was positioned in the positioning step S2.

Next, in the retrieving step S8, the expansion member 6 is contracted by setting the drug-supply port 3a, which is equipped with the two-way stopcock, of the operating portion 3 to the open state. By doing so, the drug supply device 1 is released from the secured state with respect to the inner wall of the esophagus A. Next, the drug supply device 1 is removed from the esophagus A.

In the drug supplying step S4 and the retaining step S6, the mucosal basal layer, which is the bottom-most layer of the mucosal layer in the target region R, is damaged by the drug. A scar is formed in the damaged tissue, and the tissue in the target region R contracts in the process of the scar formation. Due to this contracting action of the tissue, it is possible to cause stenosis in a portion of the region extending to the cardia D from the gastroesophageal junction C (esophagus lower portion).

As has been described above, with the drug supply device 1 according to this embodiment and a method for causing stenosis of the digestive tract by using the same, tissue below the mucous membrane of the target region R in a portion of the region extending to the cardia D from the gastroesophageal junction C (esophagus lower portion) is damaged by the drug; therefore, the invasiveness is lower and the procedure is also easier as compared with the case in which tissue is damaged by making an incision in the vicinity of the gastroesophageal junction C or by excising the tissue in the portion of the region extending to the cardia D from the gastroesophageal junction C (esophagus lower portion).

In this case, if the drug is supplied over the entire circumference of a portion of the region extending to the cardia D from the gastroesophageal junction C (esophagus lower portion), as a result of the tissue under the mucous membrane of the portion of the region extending to the cardia D from the gastroesophageal junction C (esophagus lower portion) being damaged by the drug over the entire region in the circumferential direction, excessive stenosis may occur in the portion of the region extending to the cardia D from the gastroesophageal junction C (esophagus lower portion).

In contrast, with this embodiment, the drug sheet 7 is provided in an area that does not reach the entire circumference of the expansion member 6 and is configured so as to supply the drug impregnating the drug sheet 7 to the target region R by means of contact with the drug sheet 7. Therefore, the drug is prevented from being unintentionally supplied to a region other than the target region R, and the drug is supplied only to the target region R that is in firm contact with the drug sheet 7. Accordingly, it is possible to prevent excessive stenosis from occurring in the portion of the region extending to the cardia D from the gastroesophageal junction C (esophagus lower portion) as a result of preventing the mucosal basal layer from being damaged over the entire region in the circumferential direction of the portion of the region extending to the cardia D from the gastroesophageal junction C (esophagus lower portion), and thus, it is possible to cause moderate stenosis in the portion of the region extending to the cardia D from the gastroesophageal junction C (esophagus lower portion).

Furthermore, as a result of the expansion member 6 and the drug sheet 7 being secured with respect to the esophagus A by means of the mouthpiece 3c, position displacement of the drug sheet 7 due to peristalsis of the esophagus A and gravity is prevented during the retaining period. Accordingly, it is possible to reliably continue supplying the drug to the target region R over the prescribed period.

Second Embodiment

Next, a drug supply device according to a second embodiment of the present invention will be described with reference to the drawings. In this embodiment, configurations that are shared with the first embodiment are assigned the same reference signs, descriptions thereof will be omitted, and configurations that are different from those of the first embodiment will be described.

Figure 5A:
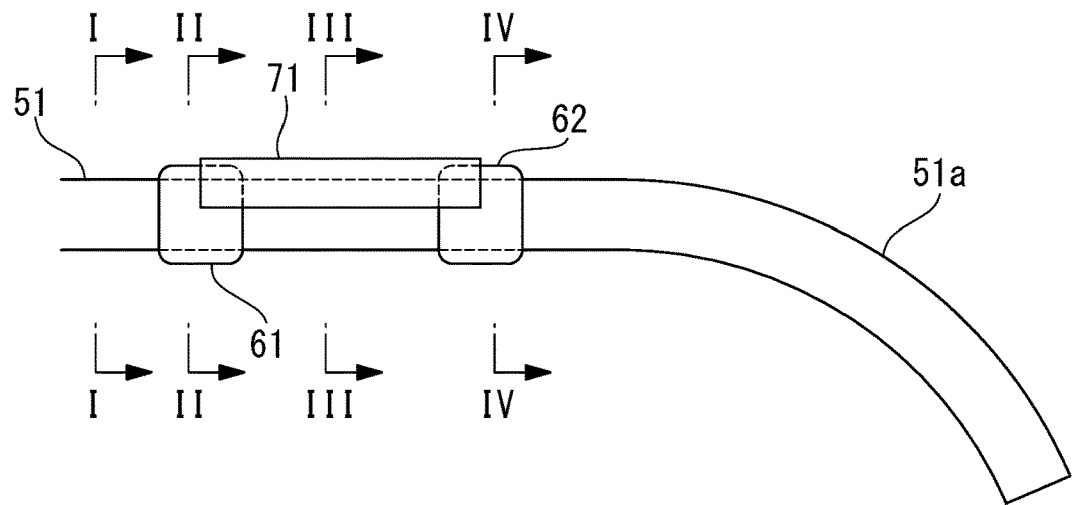
FIG. 5A is a configuration diagram of a distal-end portion of a drug supply device according to a second embodiment of the present invention.
Figure 5B:
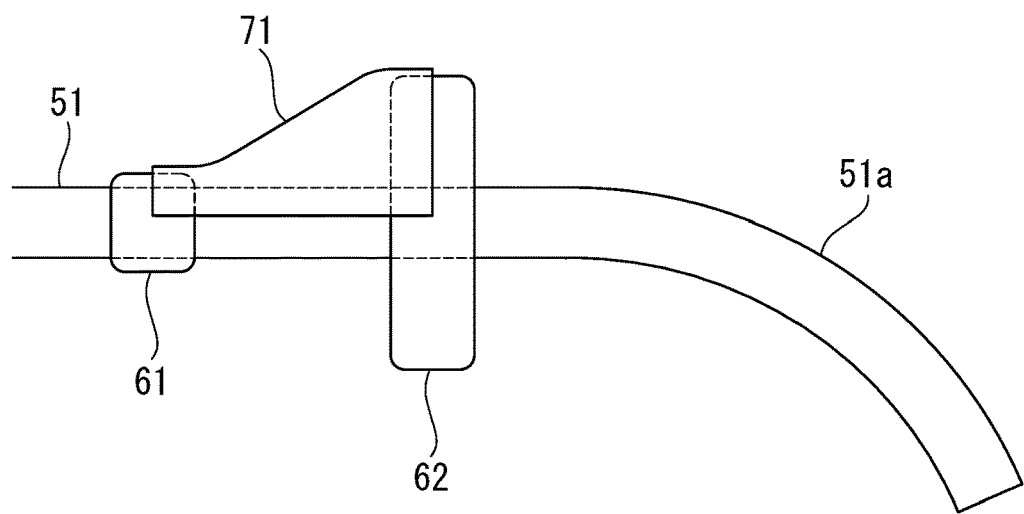
FIG. 5B is a diagram showing the distal-end portion of the drug supply device in FIG. 5A in a state in which a second expansion member is expanded.
Figure 5C:
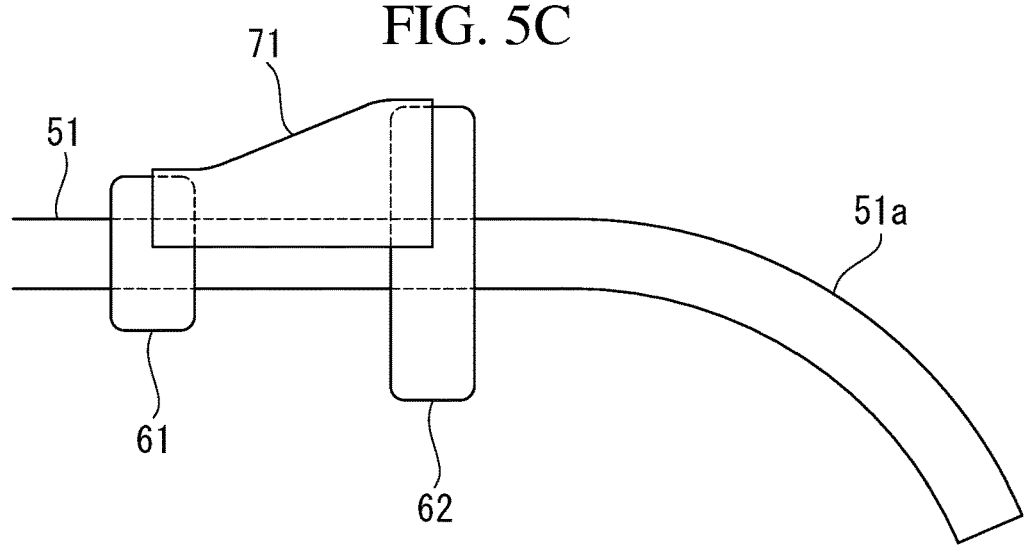
FIG. 5C is a diagram showing the distal-end portion of the drug supply device in FIG. 5A in a state in which a first expansion member and the second expansion member are expanded.

As shown in FIGS. 5A to 5C, the drug supply device according to this embodiment includes: an elongated overtube 51 into which the insertion portion 20 of the flexible endoscope can be inserted and that has a longitudinal axis; a first expansion member 61 and a second expansion member 62 that are positioned on a distal-end side of the overtube 51 and that are secured to an outer circumferential surface of the overtube 51; and a masking member 71.

The overtube (tube body) 51 has an inner diameter that is greater than the outer diameter of the insertion portion 20 of the endoscope, and, inside the overtube 51, the insertion portion 20 of the endoscope can be moved in the longitudinal direction and can be rotated about the longitudinal axis. The overtube 51 has, farther on a distal-end side than the expansion members 61 and 62 are, a distal-end portion 51a that is bent in an arc shape in a natural state and that can be elastically deformed into a linear shape.

Each of the expansion members 61 and 62 is, for example, a balloon. The overtube 51 passes through the expansion members 61 and 62, and the expansion members 61 and 62 are provided around the entire circumference of the overtube 51. The first expansion member 61 and the second expansion member 62 are provided with a spacing between each other in a direction along the longitudinal axis of the overtube 51, and the second expansion member 62 is positioned farther on the distal-end side than the first expansion member 61 is. Each of the first expansion member 61 and the second expansion member 62 can be elastically deformed between a contracted shape, indicated in FIG. 5A, and an expanded shape, indicated in FIG. 5C, as a result of being expanded and contracted with respect to the longitudinal axis of the over tube 51 in a radial direction that is orthogonal to the longitudinal axis of the overtube 51. The outer diameters of the respective expansion members 61 and 62 in the contracted shape are smaller than the inner diameter of the esophagus A. The first expansion member 61 can be expanded to a first outer diameter that is equivalent to or greater than the inner diameter of the esophagus A. The second expansion member 62 can be expanded to a second outer diameter that is even greater than the first outer diameter of the expanded first expansion member 61.

The masking member 71 is a partially cylindrical member that is formed in a semicircular arc shape or an arch shape in a lateral cross-section that is orthogonal to the longitudinal axis. The masking member 71 extends in a direction along the longitudinal axis of the overtube 51 between the first expansion member 61 and the second expansion member 62, a distal-end portion of the masking member 71 is connected to an outer surface of the second expansion member 62, and a proximal-end portion of the masking member 71 is connected to an outer surface of the first expansion member 61. The masking member 71 is provided on the opposite side from the bending direction of the distal-end portion 51a of the overtube 51.

The masking member 71 is, for example, an elastic film that freely expands and contracts in a direction along the longitudinal axis and in a circumferential direction about the longitudinal axis. As shown in FIG. 5C, the masking member 71 moves radially outward with respect to the longitudinal axis of the overtube 51 while being stretched in the direction along the longitudinal axis and in the circumferential direction in association with the expansion of the first expansion member 61 and the second expansion member 62. In the state in which the expansion members 61 and 62 both are expanded, the masking member 71 is stretched between the first expansion member 61 and the second expansion member 62.

As shown in FIGS. 6A to 6D, the overtube 51 has a first air feeding lumen 51b, a second air feeding lumen 51c, a drug lumen (channel) 51d and an endoscope lumen 51e. These four lumens 51b, 51c, 51d, and 51e extend in a direction along the longitudinal axis of the overtube 51 and are positioned independently of each other.

Figure 6A:
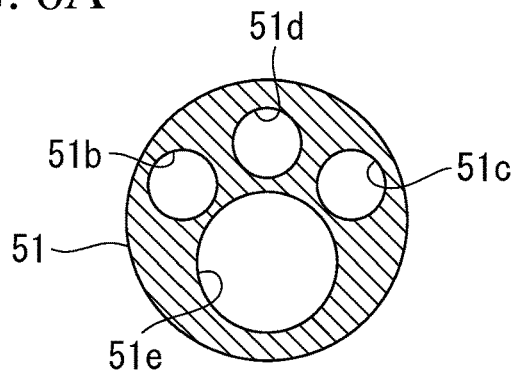
FIG. 6A is a diagram of an end face taken along line I-I in FIG. 5A.
Figure 6B:
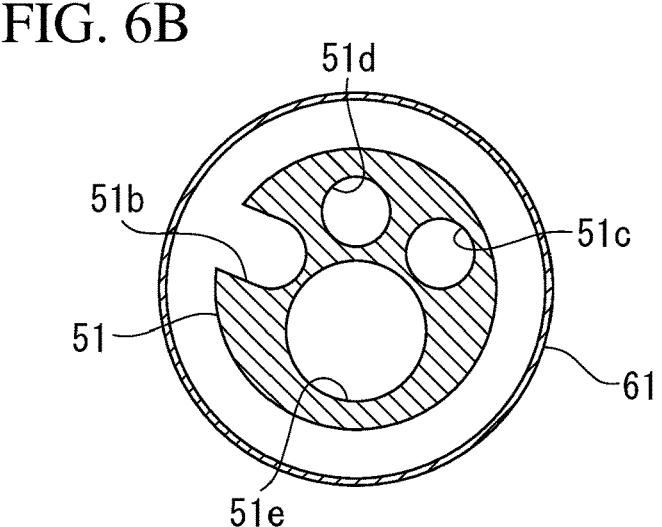
FIG. 6B is a diagram of an end face taken along line II-II in FIG. 5A.
Figure 6C:
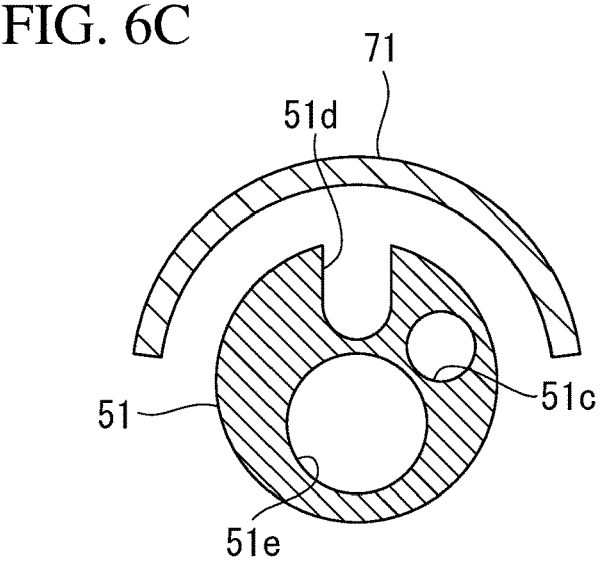
FIG. 6C is a diagram of an end face taken along line III-III in FIG. 5A.
Figure 6D:
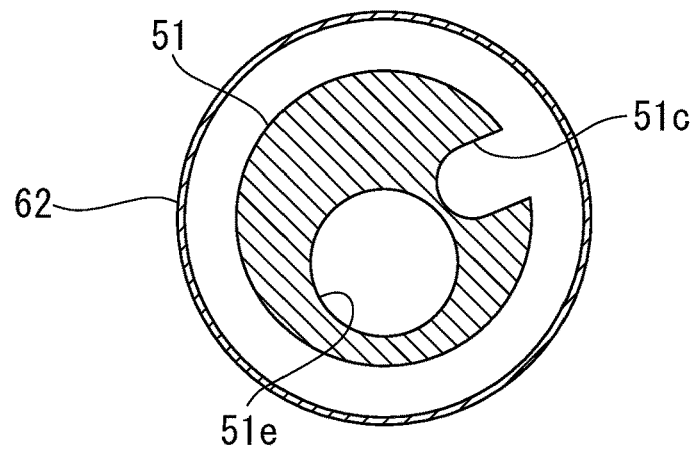
FIG. 6D is a diagram of an end face taken along line IV-IV in FIG. 5A.

As shown in FIG. 6B, a distal-end opening of the first air feeding lumen 51b opens into the interior of the first expansion member 61. As shown in FIG. 6D, a distal-end opening of the second air feeding lumen 51c opens into the interior of the second expansion member 62. As shown in FIG. 6C, a distal-end opening (outlet) of the drug lumen 51d is provided in an outer circumferential surface of the overtube 51 between the first expansion member 61 and the second expansion member 62. The drug lumen 51d is in communication with the distal-end opening and a liquid drug passes inside the drug lumen 51d.

An inflator is connected to a proximal-end opening of each of the first air feeding lumen 51b and the second air feeding lumen 51c. A cylinder is connected to a proximal-end opening of the drug lumen 51d. The endoscope lumen 51e has openings in the distal-end surface and the proximal-end surface of the overtube 51.

Next, a method for causing stenosis of the digestive tract by using the drug supply device according to this embodiment will be described.

Figure 7A:
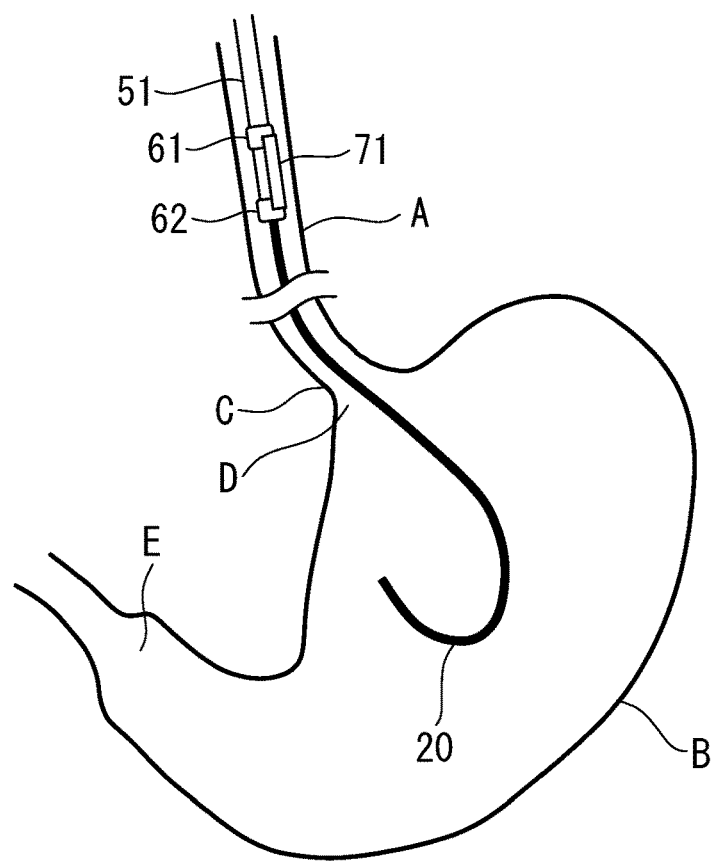
FIG. 7A is a diagram for explaining a method for causing stenosis of the digestive tract, by employing the drug supply device in FIG. 5A.
Figure 7B:
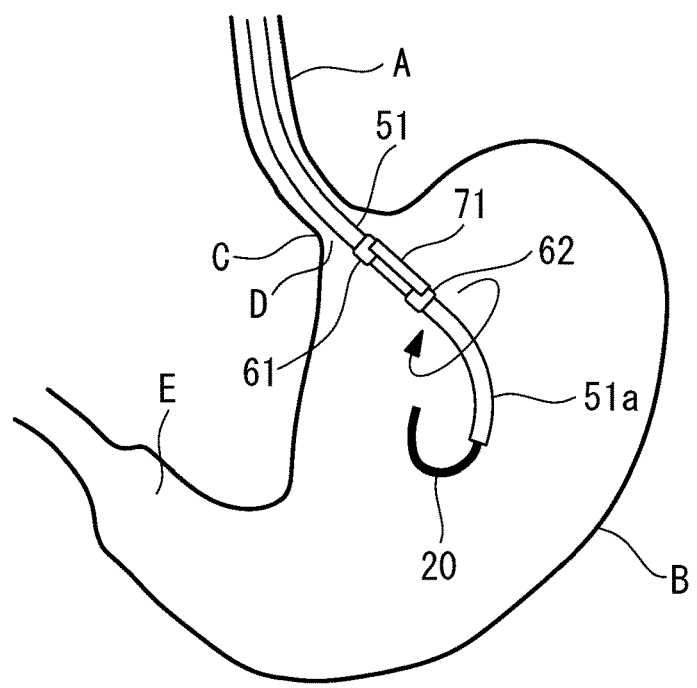
FIG. 7B is a diagram for explaining the method for causing stenosis of the digestive tract, by employing the drug supply device in FIG. 5A.

In the inserting step S1, as shown in FIG. 7A, the insertion portion 20 of the endoscope is inserted into the digestive tract from the mouth of a subject, and the bending portion of the insertion portion 20 is bent by about 180°, thereby looking up the esophagus A from the stomach B. Subsequently, as shown in FIG. 7B, the overtube 51 is inserted into the digestive tract along the insertion portion 20 inside the endoscope lumen 51e.

Next, in the positioning step S2, the masking member 71 is positioned with respect to a masking region by means of an advancing/retracting operation of the drug supply device and a rotating operation thereof about the longitudinal axis so that the masking member 71 faces a region (masking region) other than the target region.

Specifically, the overtube 51 is moved farther forward toward the distal end of the insertion portion 20. In the state in which the bending portion of the insertion portion 20 is bent, the overtube 51 passively rotates about the longitudinal axis with respect to the insertion portion 20 until the bending direction of the distal-end portion 51a is aligned with the bending direction of the bending portion of the insertion portion 20 when the distal-end portion 51a of the overtube 51 passes through the bending portion of the insertion portion 20. In other words, in the state in which the distal-end portion 51a of the overtube 51 is positioned at the bending portion of the insertion portion 20, an inner circumferential surface of the distal-end portion 51a receives a force from an outer wall of the insertion portion 20, and thus the bending direction is forcedly restricted by this force. Because of this, the overtube 51 passively rotates about the longitudinal axis with respect to the insertion portion 20 until the bending direction of the distal-end portion 51a is aligned with the bending direction of the bending portion of the insertion portion 20.

Figure 7C:
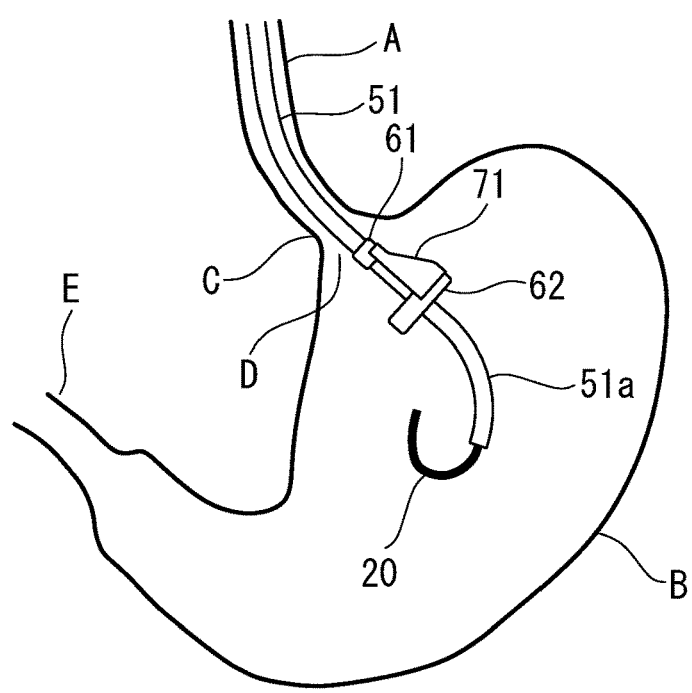
FIG. 7C is a diagram for explaining the method for causing stenosis of the digestive tract, by employing the drug supply device in FIG. 5A.

Next, as shown in FIG. 7C, by supplying a gas into the second expansion member 62 via the second air feeding lumen 51c, the second expansion member 62 is expanded. At this time, the first expansion member 61 is not expanded.

Figure 7D:
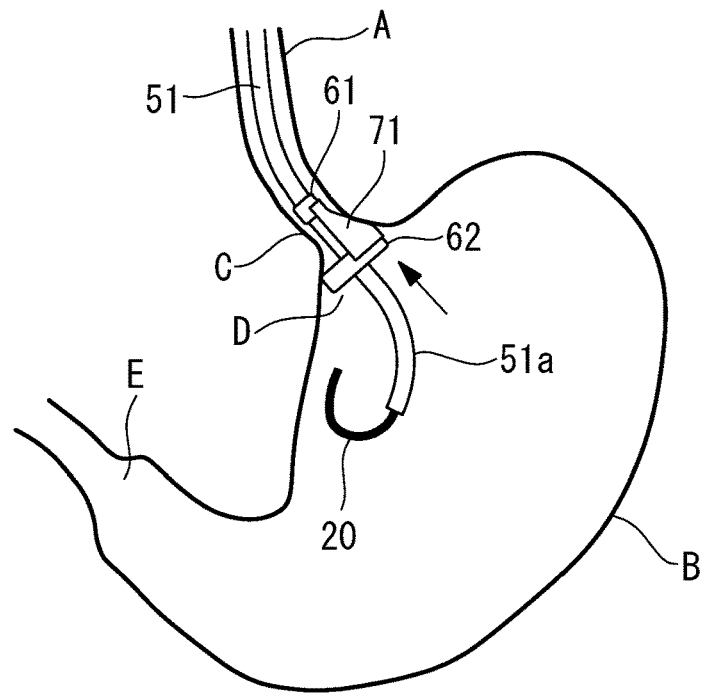
FIG. 7D is a diagram for explaining the method for causing stenosis of the digestive tract, by employing the drug supply device in FIG. 5A.

Next, as shown in FIG. 7D, the insertion portion 20 and the overtube 51 are pulled together toward the proximal end while maintaining the bending portion of the insertion portion 20 in a bent state, and thus, the second expansion member 62 in the expanded shape is pressed against the cardia D.

Figure 7E:
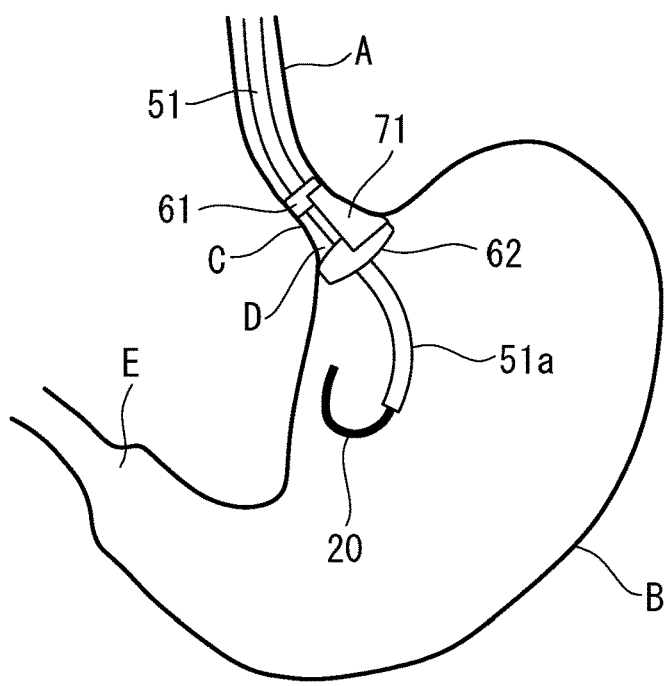
FIG. 7E is a diagram for explaining the method for causing stenosis of the digestive tract, by employing the drug supply device in FIG. 5A.

Next, in the securing step S3, as shown in FIG. 7E, by supplying the gas into the first expansion member 61 via the first air feeding lumen 51b, the first expansion member 61 is expanded. As a result, the masking member 71 is brought into firm contact with the masking region, which is a portion of the region extending to the cardia D from the gastroesophageal junction C, in the inner wall of the digestive tract. Because the first expansion member 61 and the second expansion member 62 in the expanded shape are in firm contact with the inner wall of the digestive tract, an airtight space is formed between the first expansion member 61 in the expanded shape and the second expansion member 62 in the expanded shape, and a state in which the masking member 71 is set in the masking region is also achieved. In this state, as a result of the first expansion member 61 and the second expansion member 62 being expanded, the masking member 71 is pressed against and secured at the digestive tract (the portion of the region extending to the cardia D from the gastroesophageal junction C).

Figure 7F:
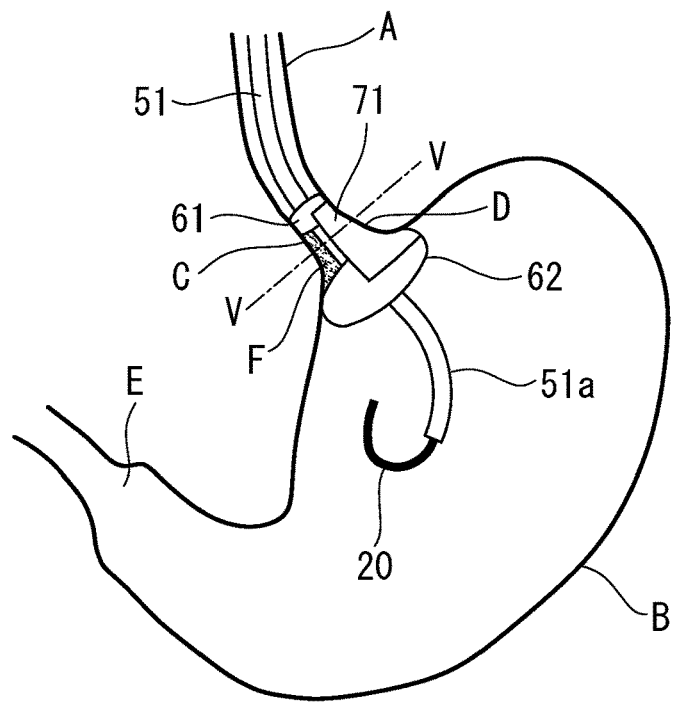
FIG. 7F is a diagram for explaining the method for causing stenosis of the digestive tract, by employing the drug supply device in FIG. 5A.
Figure 8:
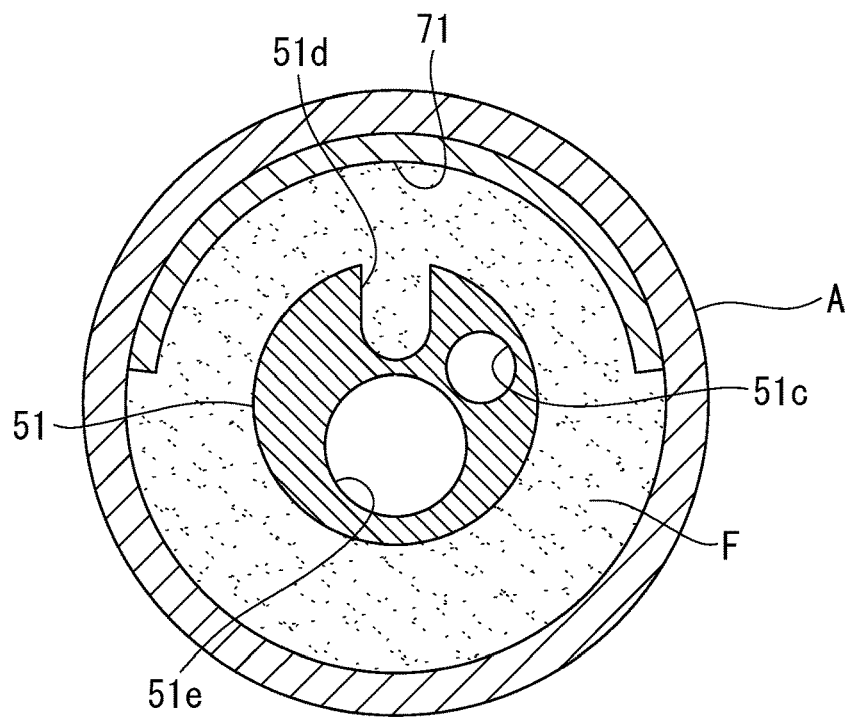
FIG. 8 is a cross-sectional view taken along line V-V in FIG. 7F.

Next, in the drug supplying step S4, as shown in FIG. 7F, a drug F is supplied into the airtight space between the first expansion member 61 and the second expansion member 62 via the drug lumen 51d. The drug F that has been discharged from the distal-end opening of the drug lumen 51d is held in the airtight space between the first expansion member 61 and the second expansion member 62. As shown in FIG. 8, because the masking member 71 is in firm contact with the inner wall of the digestive tract, the drug F is supplied only to the target region that is not covered with the masking member 71 in the inner wall of the digestive tract between the first expansion member 61 and the second expansion member 62 and is not supplied to the masking region covered with the masking member 71.

Next, the removing step S5, the retaining step S6, the follow-up observation step S7, and the retrieving step S8 are performed.

Thus, with this embodiment, the masking member 71 having a width that is less than the entire circumferences of the expansion members 61 and 62 is provided between the expansion members 61 and 62, and, in the state in which the expansion members 61 and 62 are expanded, the region other than the target region is covered with the masking member 71, thus being protected from the drug F. Therefore, the drug F is prevented from being unintentionally supplied to the region other than the target region R, and the drug F is supplied only to the target region R. Accordingly, it is possible to prevent excessive stenosis from occurring in the portion of the region extending to the cardia D from the gastroesophageal junction C (esophagus lower portion) as a result of preventing the mucosal basal layer from being damaged over the entire region in the circumferential direction of the portion of the region extending to the cardia D from the gastroesophageal junction C (esophagus lower portion), and thus, it is possible to cause moderate stenosis in the portion of the region extending to the cardia D from the gastroesophageal junction C (esophagus lower portion).

Third Embodiment

Next, a drug supply device according to a third embodiment of the present invention will be described with reference to the drawings. In this embodiment, configurations that are shared with the first and second embodiments are assigned the same reference signs, descriptions thereof will be omitted, and configurations that are different from those of the first and second embodiments will be described.

Figure 9A:
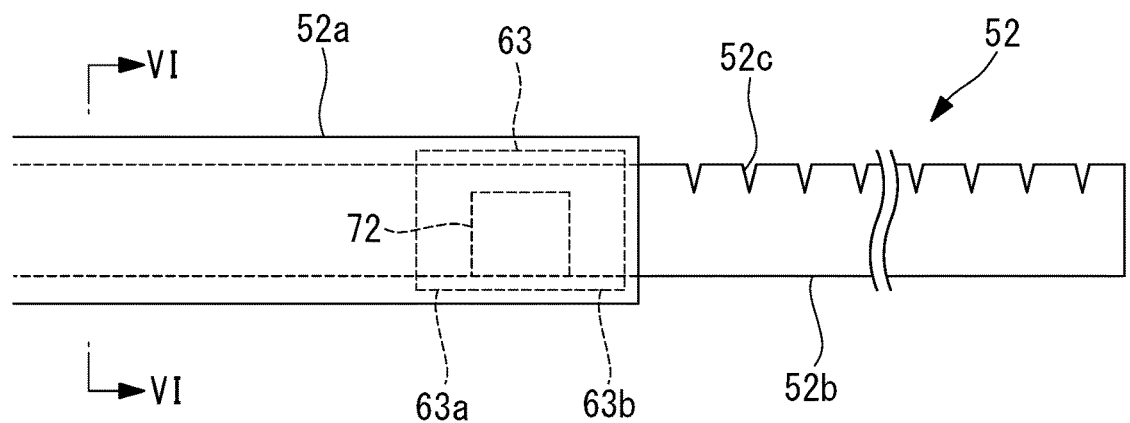
FIG. 9A is a configuration diagram of a distal-end portion of a drug supply device according to a third embodiment of the present invention.
Figure 9B:
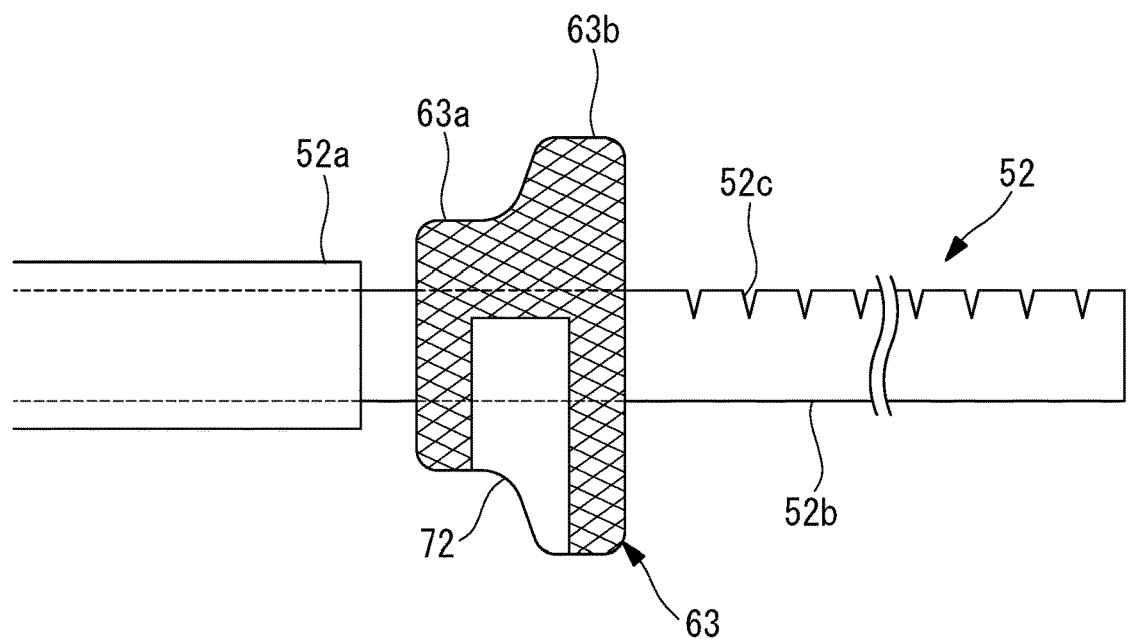
FIG. 9B is a diagram showing the distal-end portion of the drug supply device in FIG. 9A in a state in which a first expansion region and a second expansion region are expanded.
Figure 9C:
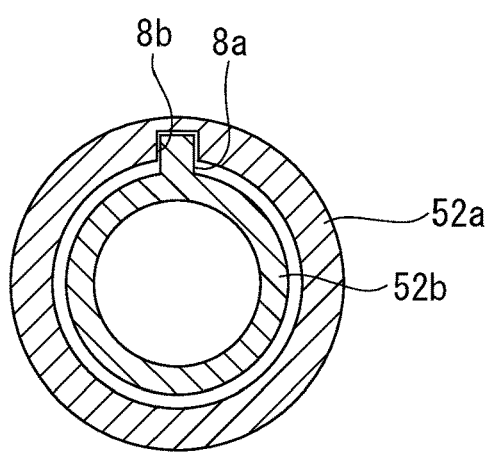
FIG. 9C is a lateral cross-sectional view taken along line VI-VI in FIG. 9A.

As shown in FIGS. 9A to 9C, the drug supply device according to this embodiment includes: an overtube 52 into which the insertion portion 20 of the flexible endoscope can be inserted; an expansion member 63 that is secured to an outer circumferential surface of the overtube 52; and a drug sheet 72 provided in the expansion member 63.

The overtube 52 includes an outer tube 52a and an inner tube (tube body) 52b disposed in the outer tube 52a along a longitudinal direction thereof. The outer tube 52a has an inner diameter that is greater than the outer diameter of the inner tube 52b, and the inner tube 52b can move in the longitudinal direction of the inner tube 52b inside the outer tube 52a. As shown in FIG. 9C, a key 8a that protrudes radially outward is provided in an outer circumferential surface of the inner tube 52b, and a key groove 8b into which the key 8a is inserted in a radial direction is formed in an inner circumferential surface of the outer tube 52a. Due to the key 8a and the key groove 8b, the outer tube 52a and the inner tube 52b are movable relative to each other in the longitudinal direction and are prevented from rotating relative to each other about the longitudinal axis.

A plurality of slits 52c that extend in the circumferential direction are formed in a distal-end portion of the inner tube 52b. The plurality of slits 52c are formed at a plurality of positions on one side in the radial direction with spacings between each other in the longitudinal direction. Accordingly, the distal-end portion of the inner tube 52b easily bends toward the opposite side from the side on which the slits 52c are formed (bends so that the slits 52c are positioned at the outside of the bent shape).

The expansion member 63 is a cylindrical stent formed from a single or a plurality of filaments. The expansion member 63 has a distal end, a proximal end, and a center axis that extends between the distal end and the proximal end, and can be expanded in the radial direction that is orthogonal to the center axis. As shown in FIG. 9A, the expansion member 63 is disposed coaxially with the tubes 52a and 52b in a cylindrical gap between the outer circumferential surface of the inner tube 52b and the inner circumferential surface of the outer tube 52a.

The expansion member 63 has a first expansion region 63a and a second expansion region 63b that is positioned farther on a distal-end side than the first expansion region 63a is and that is continuous with the first expansion region 63a. Each of the first expansion region 63a and the second expansion region 63b is self-expandable in the radial direction orthogonal to the center axis. The outer diameter of the second expansion region 63b in the expanded state is greater than the outer diameter of the first expansion region 63a in the expanded state. The first expansion region 63a and the second expansion region 63b that are sandwiched between the inner tube 52b and the outer tube 52a are held in the contracted state by the outer tube 52a. As shown in FIG. 9B, as a result of the expansion member 63 being exposed due to the movement of the outer tube 52a with respect to the inner tube 52b, each of the first expansion region 63a and the second expansion region 63b expands in the radial direction.

The drug sheet 72 is provided in an area that bridges across a distal-end portion of the first expansion region 63a and a proximal-end portion of the second expansion region 63b and that does not reach the entire circumference in the outer circumferential surface of the expansion member 63. A drug is attached to the outer surface of the drug sheet 72.

Next, a method for causing stenosis of the digestive tract by using the drug supply device according to this embodiment will be described.

Figure 10A:
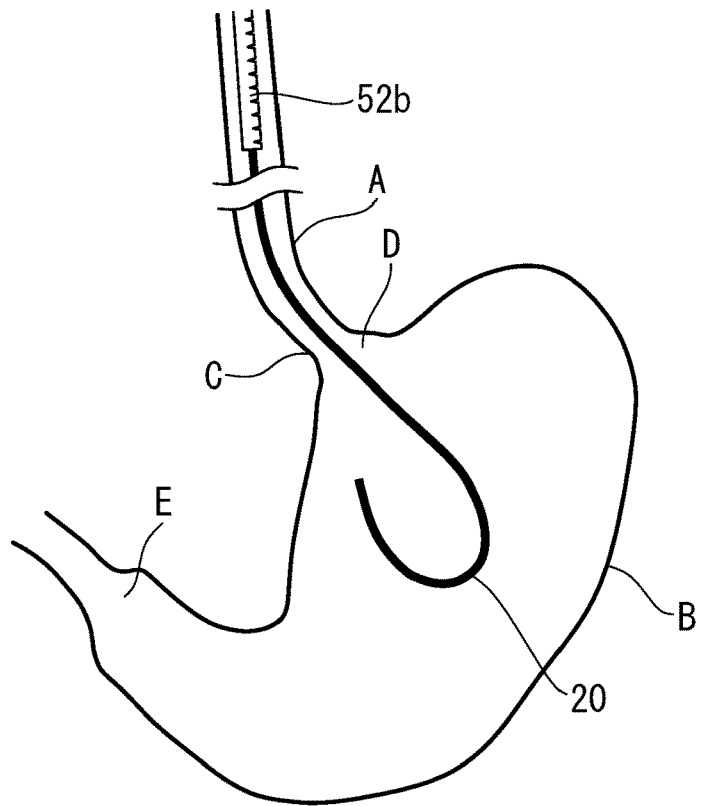
FIG. 10A is a diagram for explaining a method for causing stenosis of the digestive tract, by employing the drug supply device in FIG. 9A.

In the inserting step S1, the insertion portion 20 of the endoscope is inserted into the overtube 52 of the drug supply device in advance. Then, the drug supply device is inserted into the digestive tract from the mouth of a subject together with the endoscope. Note that the drug supply device may be inserted into the digestive tract while placing the overtube 52 along the insertion portion 20 of the endoscope after inserting the endoscope into the digestive tract from the mouth of the subject. Next, as shown in FIG. 10A, the bending portion of the insertion portion 20 is bent by about 180°, thereby looking up the esophagus A from the stomach B. Subsequently, the overtube 52 is moved forward along the insertion portion 20.

Next, in the positioning step S2, the drug sheet 72 is positioned with respect to the target region by means of an advancing/retracting operation of the drug supply device so that the drug sheet 72 faces the target region.

Figure 10B:
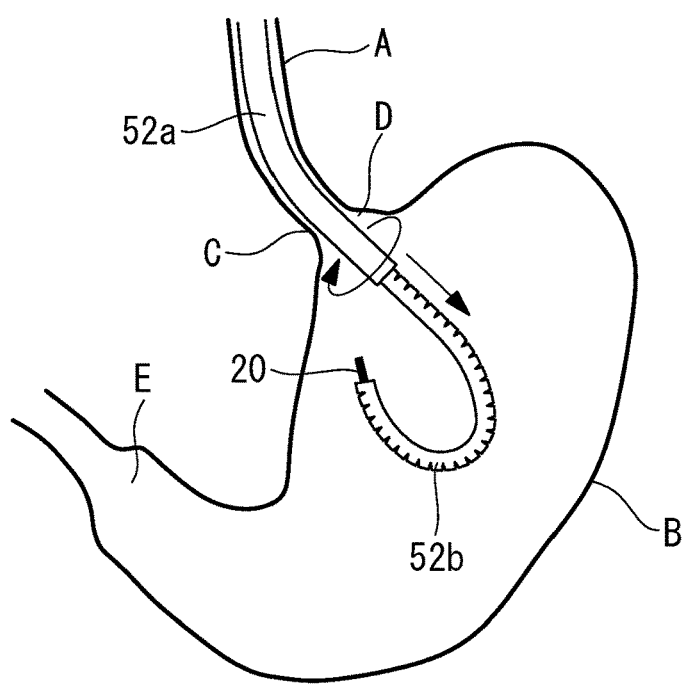
FIG. 10B is a diagram for explaining the method for causing stenosis of the digestive tract, by employing the drug supply device in FIG. 9A.

Specifically, the overtube 52 is moved farther forward along the insertion portion 20. In the state in which the bending portion of the insertion portion 20 is bent, the inner tube 52b passively rotates about the longitudinal axis with respect to the insertion portion 20 in a direction in which the slits 52c are disposed on the outside in the radial direction when the distal-end portion of the inner tube 52b passes through the bending portion of the insertion portion 20, as shown in FIG. 10B. In other words, in the state in which the distal-end portion of the inner tube 52b is positioned at the bending portion of the insertion portion 20, an inner circumferential surface of the distal-end portion of the inner tube 52b receives a force from an outer wall of the insertion portion 20, and thus the bending direction is forcedly restricted by this force. Because of this, the overtube 52 passively rotates about the longitudinal axis with respect to the insertion portion 20 until the slits 52c are disposed on the outside in the radial direction.

Figure 10C:
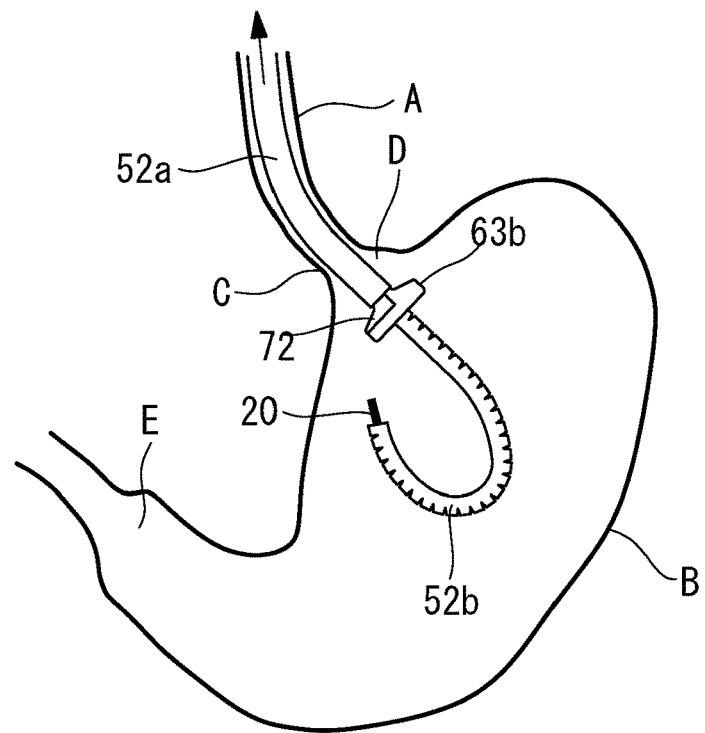
FIG. 10C is a diagram for explaining the method for causing stenosis of the digestive tract, by employing the drug supply device in FIG. 9A.

Next, as shown in FIG. 10C, by exposing the second expansion region 63b by moving the outer tube 52a toward the proximal end, the second expansion region 63b is expanded. At this time, the first expansion region 63a is not expanded.

Figure 10D:
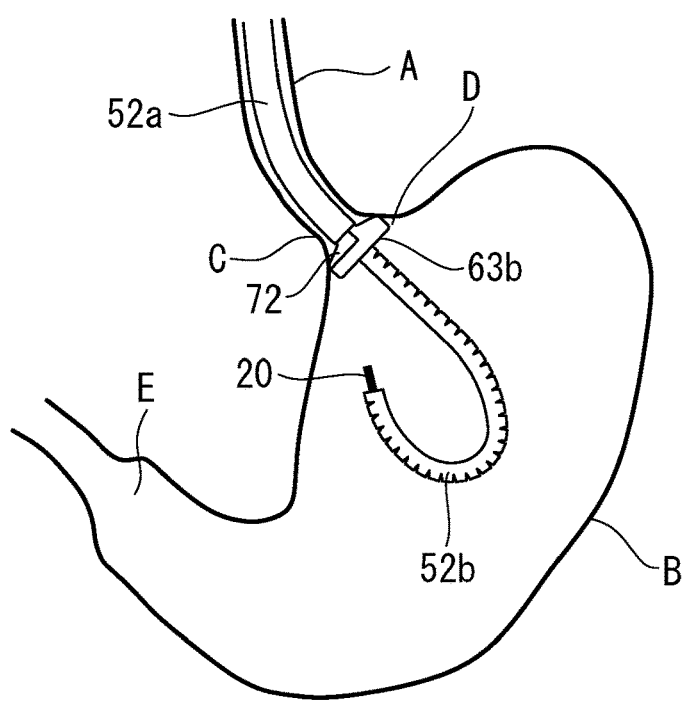
FIG. 10D is a diagram for explaining the method for causing stenosis of the digestive tract, by employing the drug supply device in FIG. 9A.

Next, as shown in FIG. 10D, the insertion portion 20 and the overtube 52 are pulled together toward the proximal end while maintaining the bending portion of the insertion portion 20 in a bent state, and thus, the second expansion region 63b in the expanded shape is pressed against the cardia D.

Figure 10E:
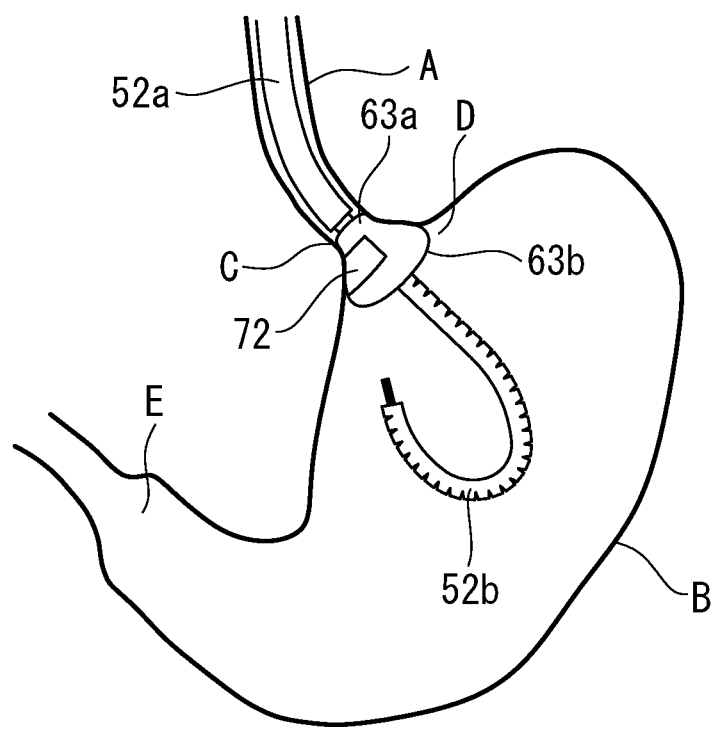
FIG. 10E is a diagram for explaining the method for causing stenosis of the digestive tract, by employing the drug supply device in FIG. 9A.

Next, in the securing step S3, as shown in FIG. 10E, by exposing the first expansion region 63a from the outer tube 52a by moving the outer tube 52a toward the proximal end, the first expansion region 63a is expanded. As a result, the drug sheet 72 is brought into firm contact with the target region, which is a portion of the region extending to the cardia D from the gastroesophageal junction C, in the inner wall of the digestive tract. In this state, as a result of the first expansion region 63a and the second expansion region 63b being expanded, the drug sheet 72 is pressed against and secured at the digestive tract (the portion of the region extending to the cardia D from the gastroesophageal junction C (esophagus lower portion)). Therefore, the drug held at the outer surface of the drug sheet 72 is supplied only to the target region R that is in firm contact with the drug sheet 72 (drug supplying step S4).

Subsequently, the removing step S5, the retaining step S6, the follow-up observation step S7, and the retrieving step S8 are performed.

Thus, with this embodiment, the drug sheet 72 is provided in an area that does not reach the entire circumference of the expansion member 63 and is configured so that the drug attached to the outer surface of the drug sheet 72 is supplied to the target region R by means of contact with the drug sheet 72. Therefore, the drug is prevented from being unintentionally supplied to a region other than the target region R, and the drug is supplied only to the target region R that is in firm contact with the drug sheet 72. Accordingly, it is possible to prevent excessive stenosis from occurring in the portion of the region extending to the cardia D from the gastroesophageal junction C (esophagus lower portion) as a result of preventing the mucosal basal layer from being damaged over the entire region in the circumferential direction of the portion of the region extending to the cardia D from the gastroesophageal junction C (esophagus lower portion), and thus, it is possible to cause moderate stenosis in the portion of the region extending to the cardia D from the gastroesophageal junction C (esophagus lower portion).

Fourth Embodiment

Next, a drug supply device according to a fourth embodiment of the present invention will be described with reference to the drawings. In this embodiment, configurations that are shared with the first to third embodiments are assigned the same reference signs, descriptions thereof will be omitted, and configurations that are different from those of the first to third embodiments will be described.

Figure 11A:
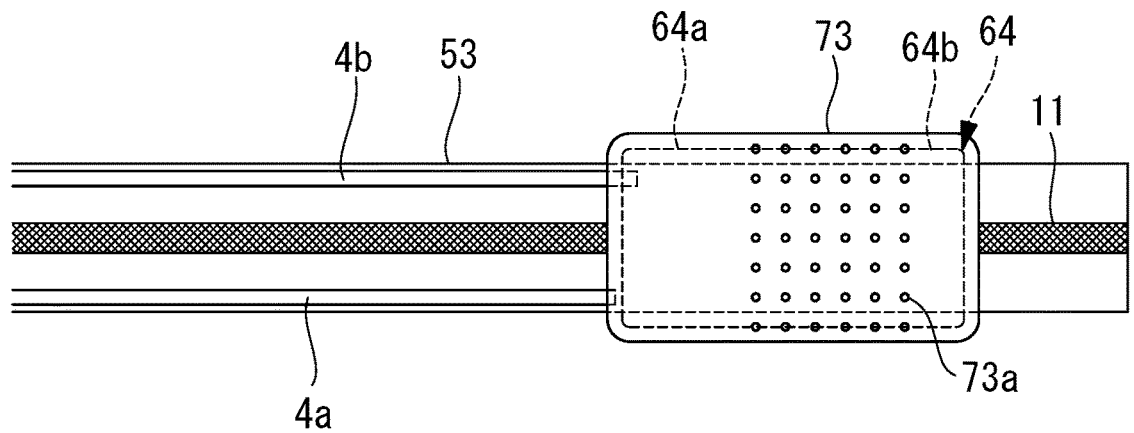
FIG. 11A is a configuration diagram of a distal-end portion of a drug supply device according to a fourth embodiment of the present invention.
Figure 11B:
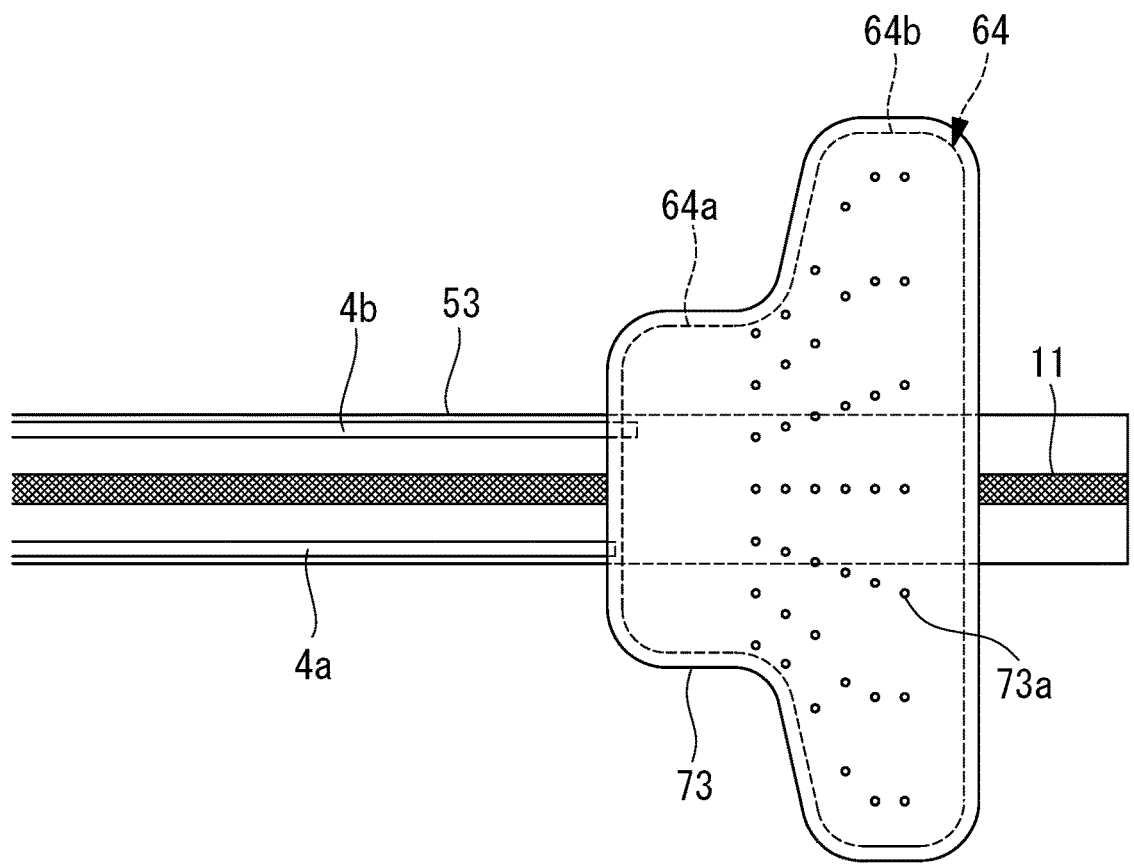
FIG. 11B is a diagram showing the distal-end portion of the drug supply device in FIG. 11A in a state in which a first expansion region and a second expansion region are expanded.

As shown in FIGS. 11A and 11B, the drug supply device according to this embodiment includes: an overtube 53 into which the insertion portion 20 of the flexible endoscope can be inserted; an expansion member 64 that is secured to an outer circumferential surface of a distal-end portion of the overtube 53; a mesh member 73 that covers the expansion member 64; a liquid feeding tube (channel) 4a; and an air feeding tube 4b.

The overtube 53 has an inner diameter that is greater than the outer diameter of the insertion portion 20, and, inside the overtube 53, the insertion portion 20 can be moved in the longitudinal direction and can be rotated about the longitudinal axis.

The expansion member 64 is, for example, a balloon. The expansion member 64 has a distal end, a proximal end, and a center axis that extends between the distal end and the proximal end, and can be expanded in a radial direction that is orthogonal to the center axis. The expansion member 64 has a first expansion region 64a and a second expansion region 64b that is positioned farther on a distal-end side than the first expansion region 64a is and that is continuous with the first expansion region 64a. The first expansion region 64a and the second expansion region 64b are respectively configured in the same manners as the first expansion region 6a and the second expansion region 6b in the first embodiment.

The mesh member 73 is a bag-like member that is disposed outside the expansion member 64 and that covers the entire outer surface of the expansion member 64. The mesh member 73 can be expanded in a direction along the surface thereof, and expands and contracts in association with the expansion and contraction of the expansion member 64. The mesh member 73 is disposed so as to form a gap with respect to the outer surface of the expansion member 64, thus ensuring a space for retaining the liquid drug between an inner surface of the mesh member 73 and the outer surface of the expansion member 64.

The mesh member 73 has a plurality of small holes 73a that are provided in the outer surface thereof and that are in communication with the space. The small holes 73a are provided in an area that bridges across a distal-end portion of the first expansion region 64a and a proximal-end portion of the second expansion region 64b and that does not reach the entire circumference in the outer surface of the mesh member 73. The space between the inner surface of the mesh member 73 and the outer surface of the expansion member 64 is airtight except for the small holes 73a and the distal-end opening of the liquid feeding tube 4a.

Figure 11C:
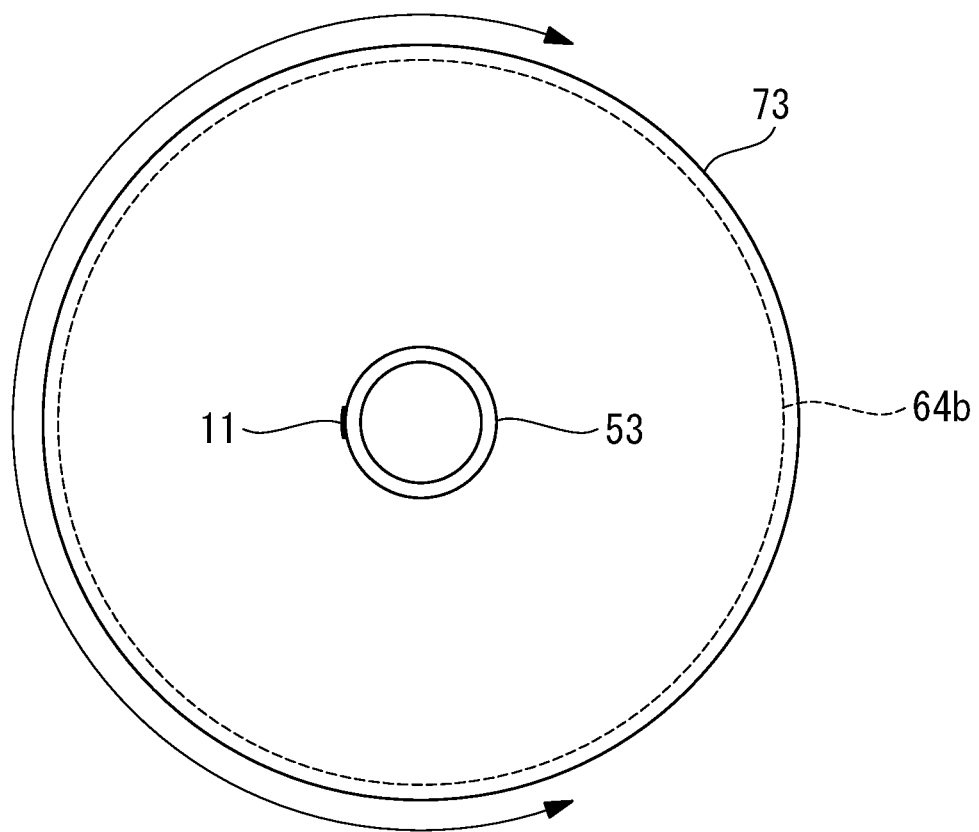
FIG. 11C is a front view of the drug supply device in FIG. 11A, as viewed from the distal-end side thereof, in a state in which the second expansion region is expanded.

A marker (indicator) 11 that indicates the positions of the small holes 73a in the circumferential direction about the longitudinal axis is provided in the outer circumferential surface of the overtube 53. The marker 11 is a line that extends along the longitudinal direction of the overtube 53. The width of the marker 11 in the circumferential direction of the overtube 53 is equal to or less than half the outer circumference of the overtube 53. As shown in FIG. 11C, in the circumferential direction, the center of the marker 11 is positioned at the center of the area in which the small holes 73a are provided (the area indicated by arrow).

The distal-end opening (outlet) of the liquid feeding tube 4a opens into the space between the inner surface of the mesh member 73 and the outer surface of the expansion member 64. The lumen of the liquid feeding tube 4a is in communication with the distal-end opening, and the liquid drug passes through inside the liquid feeding tube 4a. A syringe is connected to the proximal-end opening of the liquid feeding tube 4a.

The distal-end opening of the air feeding tube 4b opens into the interior space of the expansion member 64. An inflator is connected to the proximal-end opening of the air feeding tube 4b.

Next, a method for causing stenosis of the digestive tract by using the drug supply device according to this embodiment will be described.

Figure 12A:
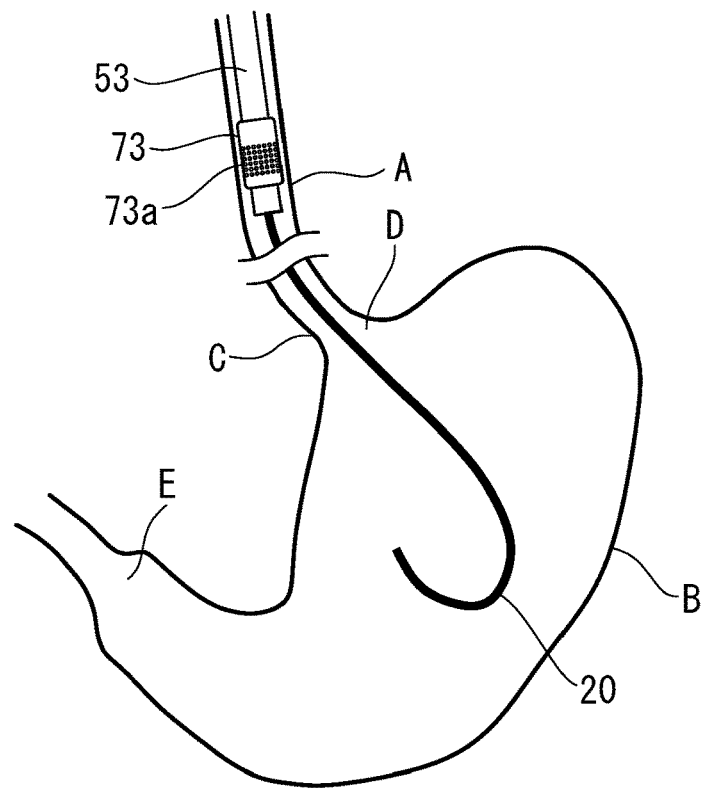
FIG. 12A is a diagram for explaining a method for causing stenosis of the digestive tract, by employing the drug supply device in FIG. 11A.

In the inserting step S1, as shown in FIG. 12A, the insertion portion 20 of the endoscope is inserted into the digestive tract from the mouth of a subject, and the bending portion of the insertion portion 20 is bent by about 180°, thereby looking up the esophagus A from the stomach B. Subsequently, as shown in FIG. 12B, the overtube 53 is inserted into the digestive tract along the insertion portion 20.

Next, in the positioning step S2, the area in which the small holes 73a are provided is positioned with respect to a target region R by means of an advancing/retracting operation of the drug supply device and a rotating operation thereof about the longitudinal axis so that the area in which the small holes 73a are provided faces the target region.

Figure 12B:
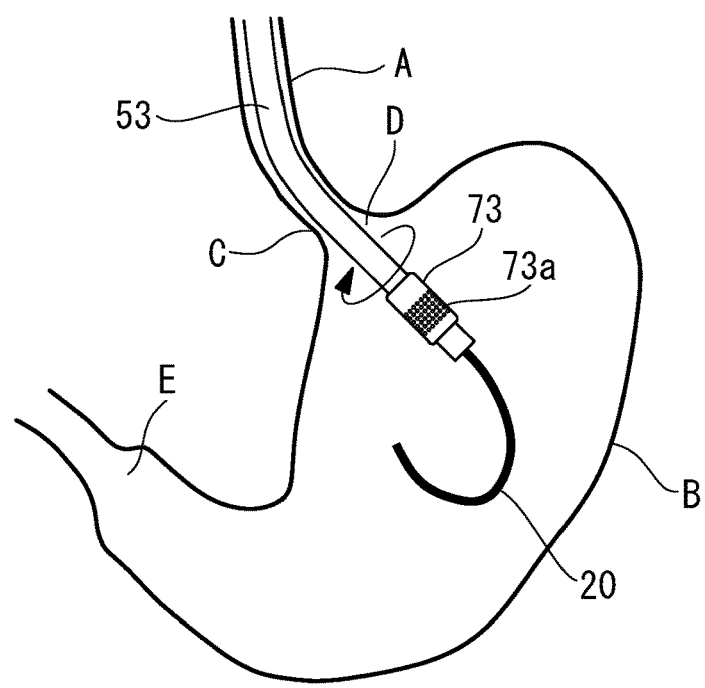
FIG. 12B is a diagram for explaining the method for causing stenosis of the digestive tract, by employing the drug supply device in FIG. 11A.
Figure 13:
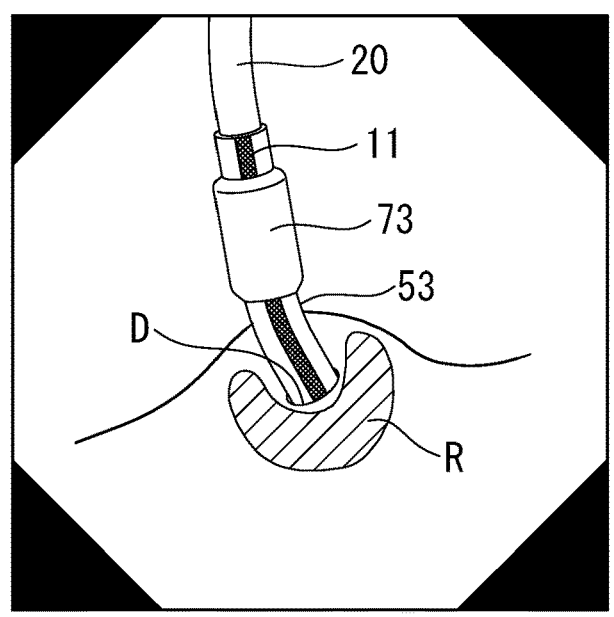
FIG. 13 is a diagram showing an example of an image acquired by means of an endoscope in the step indicated in FIG. 12B.

Specifically, as shown in FIG. 12B, by twisting the overtube 53 about the longitudinal axis, the area in which the small holes 73a are provided is positioned with respect to the target region R in the circumferential direction of the esophagus A. At this time, as shown in FIG. 13, the surgeon can position the small holes 73a with respect to the target region R by observing the marker 11 by using the endoscope and by confirming the positions of the small holes 73a in the circumferential direction on the basis of the marker 11.

Figure 12C:
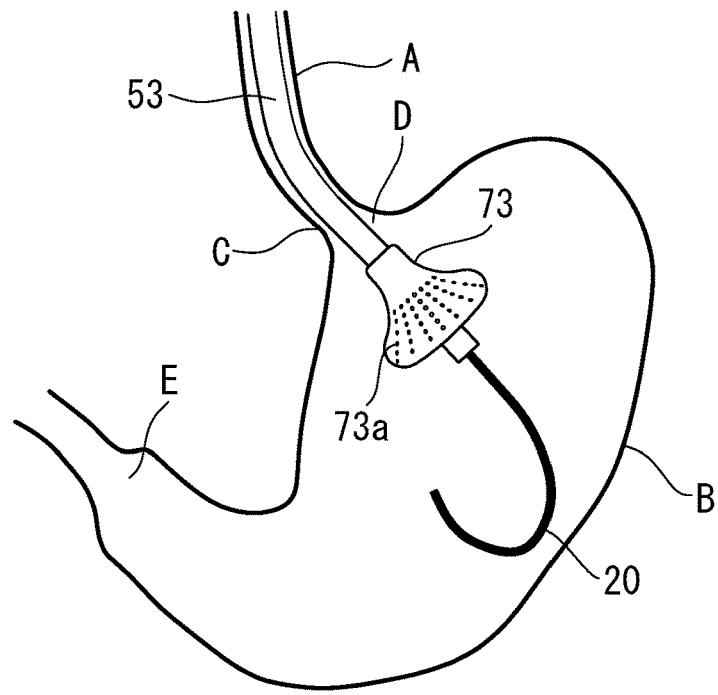
FIG. 12C is a diagram for explaining the method for causing stenosis of the digestive tract, by employing the drug supply device in FIG. 11A.
Figure 12D:
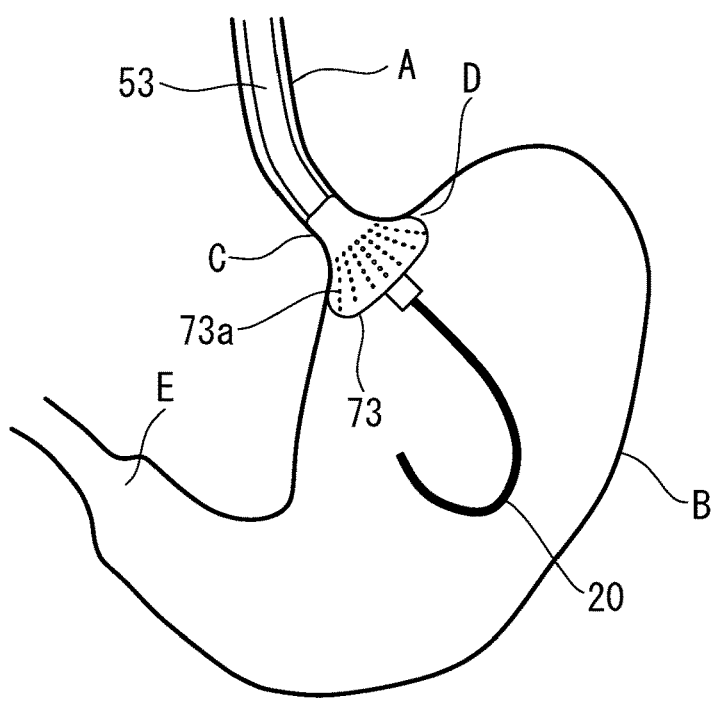
FIG. 12D is a diagram for explaining the method for causing stenosis of the digestive tract, by employing the drug supply device in FIG. 11A.
Figure 12E:
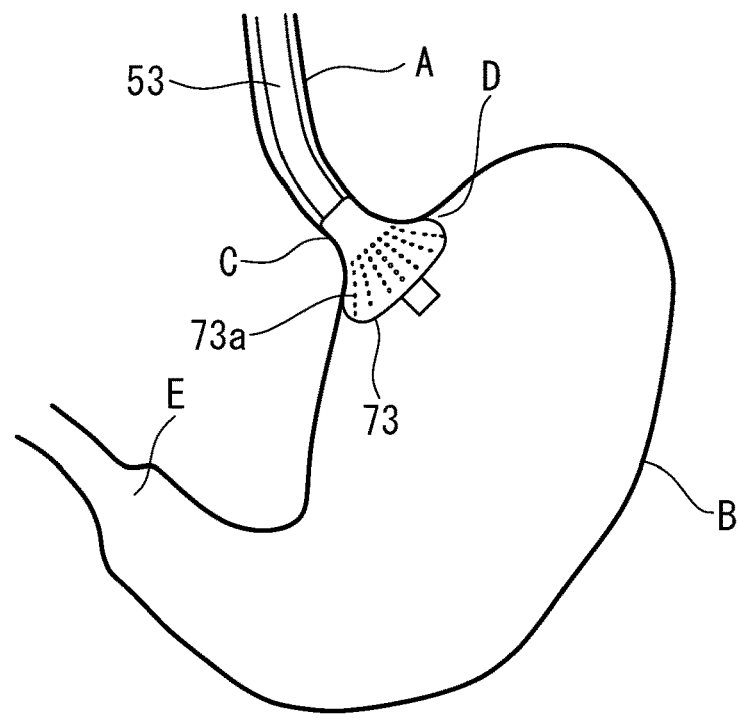
FIG. 12E is a diagram for explaining the method for causing stenosis of the digestive tract, by employing the drug supply device in FIG. 11A.

Next, by connecting the inflator to the air feeding tube 4b and by supplying a gas into the expansion member 64 from the inflator via the air feeding tube 4b, as shown in FIG. 12C, the first expansion region 64a and the second expansion region 64b are expanded until the outer diameter of the second expansion region 64b becomes greater than the inner diameter of the cardia D. Next, as shown in FIG. 12D, the insertion portion 20 and the overtube 53 are moved toward the proximal end until reaching a position at which the expanded second expansion region 64b abuts against the cardia D. Accordingly, the area in which the small holes 73a are provided is positioned with respect to the target region in the portion of the region extending to the cardia D from the gastroesophageal junction C (esophagus lower portion) in the longitudinal direction of the esophagus A.

Next, the securing step S3 is performed in the same manner as in the first embodiment.

Next, in the drug supplying step S4, the syringe containing the drug is connected to the liquid feeding tube 4a, and the drug is supplied from the syringe to the space between the mesh member 73 and the expansion member 64 via the liquid feeding tube 4a. The drug passes through the small holes 73a and leaks out to outside the mesh member 73, thus being supplied to the target region R that is in firm contact with the mesh member 73.

Next, the removing step S5, the retaining step S6, the follow-up observation step S7, and the retrieving step S8 are performed.

Thus, with this embodiment, the small holes 73a are provided in the area that does not reach the entire circumference of the mesh member 73 and are configured so as to supply the drug held in the interior of the mesh member 73 to the target region R that is in contact with the small holes 73a. Therefore, the drug is prevented from being unintentionally supplied to a region other than the target region R, and the drug is supplied only to the target region R that is in firm contact with the area in which the small holes 73a are provided in the mesh member 73. Accordingly, it is possible to prevent excessive stenosis from occurring in the portion of the region extending to the cardia D from the gastroesophageal junction C (esophagus lower portion) as a result of preventing the mucosal basal layer from being damaged over the entire region in the circumferential direction of the portion of the region extending to the cardia D from the gastroesophageal junction C (esophagus lower portion), and thus, it is possible to cause moderate stenosis in the portion of the region extending to the cardia D from the gastroesophageal junction C (esophagus lower portion).

The above-described embodiment also leads to the following aspects.

A first aspect of the present invention is a drug supply device including: a tube body having a longitudinal axis; a first expansion member that can be expanded to a first outer diameter and a second expansion member that can be expanded to a second outer diameter that is greater than the first outer diameter of the first expansion member, the first expansion member and the second expansion member being positioned on a distal-end side of the tube body and disposed with a spacing between each other in a direction along the longitudinal axis; and a masking member that includes a distal-end portion and a proximal-end portion, that extends along the longitudinal axis between the first expansion member and the second expansion member, in which the proximal-end portion is connected to an outer surface of the first expansion member, and in which the distal-end portion is connected to an outer surface of the second expansion member, wherein the tube body includes an outlet that opens between the first expansion member and the second expansion member and a channel that is in communication with the outlet and through which a liquid drug passes, the masking member is formed in an arc shape in a lateral cross-section that is orthogonal to the longitudinal axis, and, in a state in which the first expansion member and the second expansion member are expanded, the masking member stretches between the first expansion member and the second expansion member.

With this aspect, the first and second expansion members are disposed in the digestive tract so that the longitudinal axis of the tube body is placed along the longitudinal direction of the digestive tract, and the masking member is brought into firm contact with an inner wall of the digestive tract as a result of expanding the first and second expansion members. At this time, as a result of the first and second expansion members in the expanded state also being in firm contact with the inner wall of the digestive tract, the first expansion member, the second expansion member, and the masking member are secured with respect to the inner wall of the digestive tract. Next, the drug is supplied from the outlet of the channel to the space between the first expansion member and the second expansion member. The drug is accumulated in the space between the first expansion member and the second expansion member. Subsequently, as a result of retaining the expansion members in the digestive tract for a certain period of time while maintaining the state in which the masking member is in firm contact with the inner wall of the digestive tract at the same position, the drug can be continuously supplied only to a desired region (target region). In tissue of the inner wall damaged by the drug, a scar is formed in the process of healing, and peripheral tissue of the scar contracts. By utilizing this contracting action of the peripheral tissue, it is possible to cause stenosis of the digestive tract.

In this case, because the tissue of the inner wall of the digestive tract is damaged by means of the drug, the invasiveness is lower and the procedure is also easier as compared with the case in which the tissue is damaged by making an incision in the digestive tract or by excising the tissue of the digestive tract.

In addition, as a result of the movement of the drug due to gravity and peristalsis being prevented by the first and second expansion members in the expanded state, the drug is prevented from flowing out of the target region, and thus, it is possible to damage only the inner wall of the digestive tract in the desired region.

In addition, as a result of the portion in the circumferential direction in the inner wall of the digestive tract being protected by the masking member having an arc-shaped lateral cross-section, the tissue of the inner wall of the digestive tract is prevented from being damaged over the entire region in the circumferential direction, and thus, excessive stenosis is prevented. Therefore, with a simple and minimally invasive procedure, it is possible to cause stenosis of the digestive tract by causing a desired region of the digestive tract to contract.

In the above-described first aspect, each of the first expansion member and the second expansion member may be a balloon.

In the above-described first aspect, an endoscope can be inserted into the tube body, and the tube body may bend in an arc shape between a distal end of the second expansion member and the distal end of the tube body.

In the above-described first aspect, the masking member may be a film that freely expands and contracts in a direction along a surface thereof.

A second aspect of the present invention is a drug supply device including: an expansion member that includes a distal end, a proximal end, and a center axis extending between the distal end and the proximal end, and that can be expanded in a radial direction that is orthogonal to the center axis; and a drug sheet that is provided on an outer surface of the expansion member and that holds a drug, wherein the expansion member includes a first expansion region and a second expansion region that is positioned farther on a distal-end side than the first expansion region is and that is continuous with the first expansion region, and a second outer diameter of the second expansion region in an expanded state is greater than a first outer diameter of the first expansion region in an expanded state, and the drug sheet is provided in an area that bridges across a distal-end portion of the first expansion region and a proximal-end portion of the second expansion region and that does not reach an entire circumference about the center axis in the outer surface of the expansion member.

With this aspect, the expansion member is disposed in the digestive tract so that the center axis is placed along the longitudinal direction of the digestive tract, and, as a result of expanding the first and second expansion regions of the expansion member, the drug sheet is brought into firm contact with the inner wall of the digestive tract. At this time, as a result of the first and second expansion regions in the expanded state also being in firm contact with the inner wall of the digestive tract, the expansion member and the drug sheet are secured with respect to the inner wall of the digestive tract. Subsequently, as a result of retaining the expansion member in the digestive tract for a certain period of time while maintaining the state in which the drug sheet is in firm contact with the inner wall of the digestive tract at the same position, the drug can be continuously supplied only to a desired region (target region) of the inner wall from the drug sheet. In tissue of the inner wall damaged by the drug, a scar is formed in the process of healing, and peripheral tissue of the scar contracts. By utilizing this contracting action of the peripheral tissue, it is possible to cause stenosis of the digestive tract.

In this case, by disposing the expansion member at the gastroesophageal junction so that the second expansion region is disposed on the stomach side and by expanding the first and second expansion regions, the drug sheet bridging across the first and second expansion regions is brought into firm contact with the inner wall of the gastroesophageal junction. Therefore, this is particularly useful for causing stenosis of the gastroesophageal junction.

In addition, because the tissue of the inner wall of the digestive tract is damaged by means of the drug, the invasiveness is lower and the procedure is also easier as compared with the case in which the tissue is damaged by making an incision in the digestive tract or by excising the tissue of the digestive tract.

In addition, as a result of the movement of the drug due to gravity and peristalsis being prevented, the drug is prevented from flowing out of the target region, and thus, it is possible to damage only the inner wall of the digestive tract in the desired region. In addition, as a result of the drug sheet being provided in the area that does not reach the entire circumference of the expansion member, the tissue of the inner wall of the digestive tract is prevented from being damaged over the entire region in the circumferential direction, and thus, excessive stenosis is prevented. Therefore, with a simple and minimally invasive procedure, it is possible to cause stenosis of the digestive tract by causing a desired region of the digestive tract to contract.

In the above-described second aspect, the expansion member may be a balloon or a self-expanding stent.

The above-described second aspect may additionally include a tube body that includes a proximal end and a distal end and into which an endoscope can be inserted, wherein, between a distal end of the second expansion region and the distal end of the tube body, a plurality of slits that extend in a direction that is orthogonal to a longitudinal axis of the tube body are formed in the tube body with spacings between each other in a direction along the longitudinal axis.

A third aspect of the present invention is a drug supply device including: an expansion member that includes a distal end, a proximal end, and a center axis extending between the distal end and the proximal end, and that can be expanded in a radial direction that is orthogonal to the center axis; a mesh member that is disposed outside the expansion member so as to form a gap with respect to an outer surface of the expansion member and that covers the outer surface of the expansion member; and a channel that includes an outlet that opens into the gap, that is in communication with the outlet, and through which a liquid drug passes, wherein the expansion member includes a first expansion region and a second expansion region that is positioned farther on a distal-end side than the first expansion region is and that is continuous with the first expansion region, and an outer diameter of the second expansion region in an expanded state is greater than an outer diameter of the first expansion region in an expanded state, the mesh member includes a plurality of small holes that open in an outer surface of the mesh member and that are in communication with the gap, and the plurality of small holes are provided in an area that bridges across a distal-end portion of the first expansion region and a proximal-end portion of the second expansion region and that does not reach an entire circumference about the center axis in the outer surface of the mesh member.

With this aspect, the expansion member is disposed in the digestive tract so that the center axis is placed along the longitudinal direction of the digestive tract, and, as a result of expanding the first and second expansion regions of the expansion member, the mesh member is brought into firm contact with the inner wall of the digestive tract. At this time, the expansion member and the mesh member are secured with respect to the inner wall of the digestive tract by the first and second expansion regions in the expanded state. Next, the drug is supplied from the outlet of the channel to the gap between the mesh member and the expansion member. Subsequently, the expansion member is retained in the digestive tract for a certain period of time while maintaining the state in which the mesh member is in firm contact with the inner wall of the digestive tract at the same position. Because the drug seeps out to outside only from the small holes in the outer surface of the mesh member, the drug can be continuously supplied only to a desired region (target region). In tissue of the inner wall damaged by the drug, a scar is formed in the process of healing, and peripheral tissue of the scar contracts. By utilizing this contracting action of the peripheral tissue, it is possible to cause stenosis of the digestive tract.

In this case, by disposing the expansion member in the vicinity of the gastroesophageal junction so that the second expansion region is disposed on the stomach side and by expanding the first and second expansion regions, the mesh member bridging across the first and second expansion regions is brought into firm contact with an inner wall in the vicinity of the gastroesophageal junction. Therefore, this is particularly useful for causing stenosis in the vicinity of the gastroesophageal junction.

In this case, because the tissue of the inner wall of the digestive tract is damaged by means of the drug, the invasiveness is lower and the procedure is also easier as compared with the case in which the tissue is damaged by making an incision in the digestive tract or by excising the tissue of the digestive tract.

In addition, as a result of the movement of the drug due to gravity and peristalsis being prevented, the drug is prevented from flowing out of the target region, and thus, it is possible to damage only the inner wall of the digestive tract in the desired region. In addition, as a result of the small holes being provided in the area that does not reach the entire circumference of the expansion member, the tissue of the inner wall of the digestive tract is prevented from being damaged over the entire region in the circumferential direction, and thus, excessive stenosis is prevented. Therefore, with a simple and minimally invasive procedure, it is possible to cause stenosis of the digestive tract by causing a desired region of the digestive tract to contract.

In the above-described third aspect, the expansion member may be a balloon. Alternatively, the expansion member may be a stent formed from a single or a plurality of filaments.

The above-described third aspect may additionally include a tube body that includes a proximal end and a distal end and into which an endoscope can be inserted, wherein an indicator that indicates positions of the small holes in a circumferential direction about a longitudinal axis of the tube body may be provided on a distal-end side of the second expansion region. The indicator may be provided on an outer circumferential surface at the distal end of the tube body. In addition, a width of the indicator in the circumferential direction of the tube body may be equal to or less than half an outer circumference of the tube body.

REFERENCE SIGNS LIST 1 drug supply device
2 treating portion
3 operating portion
4 first tube principal body
4a liquid feeding tube (channel)
4b air feeding tube
5 second tube principal body (tube body)

51, 52 overtube
52b inner tube (tube body)
53 overtube (tube body)
6, 63, 64 expansion member
6a, 63a, 64a first expansion region
6b, 63b, 64b second expansion region
61 first expansion member
62 second expansion member
7, 72 drug sheet
71 masking member
73 mesh member
10 marker
11 marker (indicator)
20 insertion portion
A esophagus (digestive tract)
B stomach
C gastroesophageal junction
D cardia
E pylorus
F drug

The invention claimed is:

1. A device comprising:
a tube body having a longitudinal axis;
a first expansion member configured to be expanded to a first outer diameter and a second expansion member configured to be expanded to a second outer diameter that is greater than the first outer diameter of the first expansion member, the first expansion member and the second expansion member being positioned on a distal-end side of the tube body and disposed with a spacing between each other in a direction along the longitudinal axis; and
a masking member that includes a distal-end portion and a proximal-end portion, that extends along the longitudinal axis between the first expansion member and the second expansion member, in which the proximal-end portion is connected to an outer surface of the first expansion member, and in which the distal-end portion is connected to an outer surface of the second expansion member,
wherein
the masking member is formed in an arc shape in a lateral cross-section that is orthogonal to the longitudinal axis, and,
in a state in which the first expansion member and the second expansion member are expanded, the masking member stretches between the first expansion member and the second expansion member.

2. The device according to claim 1, wherein each of the first expansion member and the second expansion member is a balloon.

3. The device according to claim 1,
wherein the tube body allows an endoscope to be inserted thereinto, and
the tube body bends in an arc shape between a distal end of the second expansion member and the distal end of the tube body.

4. The device according to claim 1, wherein the masking member is a film that expands and contracts in a direction along a surface thereof.

5. The device according to claim 1, wherein the tube body includes an opening that opens between the first expansion member and the second expansion member and a channel that is in communication with the opening and through which a fluid passes.

6. A device comprising: a tube body having a longitudinal axis; a first expansion member configured to be expanded to a first outer diameter and a second expansion member configured to be expanded to a second outer diameter that is greater than the first outer diameter of the first expansion member, the first expansion member and the second expansion member being positioned on a distal-end side of the tube body and disposed with a spacing between each other in a direction along the longitudinal axis; and a masking member that includes a distal-end portion and a proximal-end portion, that extends along the longitudinal axis between the first expansion member and the second expansion member, in which the proximal-end portion is connected directly to an outer surface of the first expansion member, and in which the distal-end portion is connected directly to an outer surface of the second expansion member, wherein the tube body includes an opening positioned between the first expansion member and the second expansion member and a channel that is in communication with the opening and through which a fluid passes.

7. The device according to claim 6, wherein each of the first expansion member and the second expansion member is a balloon.

8. The device according to claim 6, wherein
the tube body allows an endoscope to be inserted thereinto, and
the tube body bends in an arc shape between a distal end of the second expansion member and the distal end of the tube body.

9. The device according to claim 6, wherein the masking member is a film that expands and contracts in a direction along a surface thereof.

10. The device according to claim 6, wherein the masking member is formed in an arc shape in a lateral cross-section that is orthogonal to the longitudinal axis.

11. The device according to claim 6, wherein in a state in which the first expansion member and the second expansion member are expanded, the masking member stretches between the first expansion member and the second expansion member.

12. The device according to claim 6, wherein
the tube body includes a bending portion at a distal-end portion thereof, the bending portion bending in a prescribed direction, and
the masking member is provided on an opposite side from a bending direction of the bending portion.

13. A device comprising: a tube body having a longitudinal axis; a first expansion member configured to be expanded to a first outer diameter and a second expansion member configured to be expanded to a second outer diameter that is greater than the first outer diameter of the first expansion member, the first expansion member and the second expansion member being positioned on a distal-end side of the tube body and disposed with a spacing between each other in a direction along the longitudinal axis; and a film that includes a distal-end portion and a proximal-end portion, that extends along the longitudinal axis between the first expansion member and the second expansion member, in which the proximal-end portion is connected directly to a part of the first expansion member, and in which the distal-end portion is connected directly to a part of the second expansion member.

14. The device according to claim 13, wherein each of the first expansion member and the second expansion member is a balloon.

15. The device according to claim 13, wherein
the tube body allows an endoscope to be inserted thereinto, and the tube body bends in an arc shape between a distal end of the second expansion member and the distal end of the tube body.

16. The device according to claim 13, wherein the film is formed in an arc shape in a lateral cross-section that is orthogonal to the longitudinal axis.

17. The device according to claim 13, wherein in a state in which the first expansion member and the second expansion member are expanded, the film stretches between the first expansion member and the second expansion member.

18. The device according to claim 13, wherein
the tube body includes a bending portion at a distal-end portion thereof, the bending portion bending in a prescribed direction, and
the film is provided on an opposite side from a bending direction of the bending portion.

19. The device according to claim 13, wherein the tube body includes an opening that opens between the first expansion member and the second expansion member and a channel that is in communication with the opening and through which a fluid passes.

\* \* \* \* \*